US007378078B2

(12) United States Patent
Ross et al.

(10) Patent No.: US 7,378,078 B2
(45) Date of Patent: May 27, 2008

(54) COMPOSITIONS AND METHODS FOR DETECTING PROTEOLYTIC ACTIVITY

(75) Inventors: Brian D. Ross, Ann Arbor, MI (US); Alnawaz Rehemtulla, Plymouth, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 656 days.

(21) Appl. No.: 10/452,184

(22) Filed: Jun. 2, 2003

(65) Prior Publication Data
US 2004/0053332 A1   Mar. 18, 2004

Related U.S. Application Data

(62) Division of application No. 09/737,255, filed on Dec. 13, 2000, now abandoned.

(51) Int. Cl.
A61K 49/00 (2006.01)
A61K 38/48 (2006.01)
A61B 5/00 (2006.01)
A01N 63/00 (2006.01)
C12P 21/04 (2006.01)
C12N 15/00 (2006.01)
C12N 5/00 (2006.01)

(52) U.S. Cl. ............... 424/9.1; 424/9.321; 424/9.6; 424/93.1; 424/94.63; 435/69.7; 435/320.1; 435/325; 435/455

(58) Field of Classification Search ............... None
See application file for complete search history.

(56) References Cited

U.S. PATENT DOCUMENTS

| | | | |
|---|---|---|---|
| 4,458,066 A | 7/1984 | Caruthers et al. |
| 4,558,279 A | 12/1985 | Ackerman et al. |
| 4,731,239 A | 3/1988 | Gordon |
| 4,906,931 A | 3/1990 | Sepponen |
| 4,952,493 A | 8/1990 | Kettner et al. |
| 4,985,678 A | 1/1991 | Gangarosa et al. |
| 5,031,624 A | 7/1991 | Mistretta et al. |
| 5,094,939 A | 3/1992 | Okada et al. |
| 5,098,828 A | 3/1992 | Geiger et al. |
| 5,103,098 A | 4/1992 | Fenyves |
| 5,109,397 A | 4/1992 | Gordon et al. |
| 5,207,222 A | 5/1993 | Koizumi et al. |
| 5,208,581 A | 5/1993 | Collins |
| 5,210,421 A | 5/1993 | Gullberg et al. |
| 5,214,382 A | 5/1993 | Harms et al. |
| 5,229,285 A | 7/1993 | Kajiyama et al. |
| 5,272,343 A | 12/1993 | Stearns |
| 5,360,728 A | 11/1994 | Prasher |
| 5,378,987 A | 1/1995 | Ishihara et al. |
| 5,406,479 A | 4/1995 | Harman |
| 5,422,426 A | 6/1995 | DiMarchi et al. |
| 5,446,799 A | 8/1995 | Tuy |
| 5,450,010 A | 9/1995 | Van Der Meulen et al. |
| 5,455,512 A | 10/1995 | Groen et al. |
| 5,532,489 A | 7/1996 | Yamashita et al. |
| 5,552,157 A | 9/1996 | Yagi et al. |
| 5,555,251 A | 9/1996 | Kinanen |
| 5,573,933 A | 11/1996 | Seamark et al. |
| 5,595,885 A | 1/1997 | Stetler-Stevenson et al. |
| 5,600,145 A | 2/1997 | Plummer |
| 5,608,221 A | 3/1997 | Bertelsen et al. |
| 5,639,940 A | 6/1997 | Garner et al. |
| 5,648,218 A | 7/1997 | Stults |
| 5,650,135 A | 7/1997 | Contag et al. |
| 5,736,129 A | 4/1998 | Medenica et al. |
| 5,744,320 A | 4/1998 | Sherf et al. |
| 5,846,768 A | 12/1998 | Abrams et al. |
| 5,858,715 A | 1/1999 | Hillman et al. |
| 5,861,267 A | 1/1999 | Su |
| 5,866,348 A | 2/1999 | Scheirer |
| 5,880,327 A | 3/1999 | Lubon et al. |
| 5,891,698 A | 4/1999 | Prieto et al. |
| 5,892,070 A | 4/1999 | Prieto et al. |
| 5,900,636 A | 5/1999 | Nellemann et al. |
| 5,922,854 A | 7/1999 | Kumar et al. |

(Continued)

FOREIGN PATENT DOCUMENTS

WO   WO 99/66324   12/1999

(Continued)

OTHER PUBLICATIONS

Gambhir et al., 2000, Proc. Nat. Acad. Sci. USA, 97:2785-2790.*

(Continued)

Primary Examiner—Joseph Woitach
Assistant Examiner—Kelagilnamane Hiriyanna
(74) Attorney, Agent, or Firm—Casimir Jones, S.C.

(57) ABSTRACT

The invention provides compositions and methods for non-invasive imaging of enzyme (e.g., protease) activity in cells, tissues and organs and entire bodies in vitro, in vivo and in situ. The invention provides a chimeric polypeptide having a bioluminescent or chemiluminescent polypeptide, or a heterologous kinase, and at least one silencing moiety, and a protease cleavage motif positioned between the first and second domains. The imaging can be by computer assisted tomography (CAT), magnetic resonance spectroscopy (MRS), magnetic resonance imaging (MRI), positron emission tomography (PET), single-photon emission computed tomography (SPECT), or bioluminescence imaging (BLI).

24 Claims, 10 Drawing Sheets

U.S. PATENT DOCUMENTS

| | | | |
|---|---|---|---|
| 5,925,523 | A | 7/1999 | Dove et al. |
| 5,935,931 | A | 8/1999 | Hillman et al. |
| 5,946,371 | A | 8/1999 | Lai |
| 5,955,429 | A | 9/1999 | Hillman et al. |
| 5,958,378 | A | 9/1999 | Waldrep et al. |
| 5,959,171 | A | 9/1999 | Hyttinen et al. |
| 5,976,822 | A | 11/1999 | Landrum et al. |
| 5,976,857 | A | 11/1999 | Powell et al. |
| 5,985,829 | A | 11/1999 | Harris et al. |
| 6,001,967 | A | 12/1999 | Gibson et al. |
| 6,010,853 | A | 1/2000 | Kanteti et al. |
| 6,013,278 | A | 1/2000 | Byra et al. |
| 6,017,735 | A | 1/2000 | O'Hare et al. |
| 6,037,145 | A | 3/2000 | Yabuta et al. |
| 6,060,261 | A | 5/2000 | Ryufuku et al. |
| 6,063,400 | A | 5/2000 | Geho et al. |
| 6,072,031 | A | 6/2000 | Pastan et al. |
| 6,072,177 | A | 6/2000 | McCroskey et al. |
| 6,074,859 | A | 6/2000 | Hirokawa et al. |
| 6,083,530 | A | 7/2000 | Mayer et al. |
| 6,087,476 | A | 7/2000 | Kenten et al. |
| 6,093,398 | A | 7/2000 | Khaw et al. |
| 6,107,088 | A | 8/2000 | Korneluk et al. |
| 6,107,541 | A | 8/2000 | Arnold |
| 6,110,490 | A | 8/2000 | Thierry |
| 6,111,166 | A | 8/2000 | Van de Winkel |
| 6,111,410 | A | 8/2000 | Young |
| 6,114,568 | A | 9/2000 | Andresen et al. |
| 6,115,446 | A | 9/2000 | Pan |
| 6,118,044 | A | 9/2000 | Karasuyama et al. |
| 6,119,032 | A | 9/2000 | Martin et al. |
| 6,121,775 | A | 9/2000 | Pearlman |
| 6,127,825 | A | 10/2000 | Goto |
| 6,128,522 | A | 10/2000 | Acker et al. |
| 6,132,983 | A | 10/2000 | Lowe et al. |
| 6,133,243 | A | 10/2000 | Kirn |
| 6,140,099 | A | 10/2000 | Strauss, III |
| 6,143,522 | A | 11/2000 | Helbing et al. |
| 6,143,716 | A | 11/2000 | Meers et al. |
| 6,144,202 | A | 11/2000 | Kanazawa et al. |
| 6,146,659 | A | 11/2000 | Rahman |
| 6,147,060 | A | 11/2000 | Zasloff et al. |
| 6,149,937 | A | 11/2000 | Camu et al. |
| 6,151,377 | A | 11/2000 | Nilsson |
| 6,156,952 | A | 12/2000 | Bryant et al. |

FOREIGN PATENT DOCUMENTS

| | | |
|---|---|---|
| WO | WO 00/62067 A1 | 10/2000 |
| WO | WO 00/66615 | 11/2000 |

OTHER PUBLICATIONS

Xu et al.,1998, Nucleic Acids research 26:2034-2035.*
Cohen et al., 1997, Biochem. J. 326:1-6.*
Hulboy et al., 1997, Molecular. Human. Reproduction. 3:27-45.*
Mahajan et al., 1999, Chemistry and Biology 6:401-409.*
Kown et al., 2000, Circulation 102 [suppl. III]:III-228-III-232.*
Al-Obeidi, F., et al., "Peptide and Peptidomimetic Libraries," *Molec. Biotechnol.* 9:205-223, Humana Press (1998).
Anctil, M. and Shimomura, O., "Mechanism of photoinactivation and re-activation in the bioluminescence system of the ctenophore *Mnemiopsis*,"*Biochem. J.* 221:269-272, The Biochemical Society (1984).
Baguisi, A., et al., "Production of goats by somatic cell nuclear transfer," *Nat. Biotechnol.* 17:456-461, Nature America Inc. (May 1999).
Bain, D.L., et al., "The N-terminal Region of the Human Progesterone A-receptor," *J. Biol. Chem.* 275:7313-7320, The American Society for Biochemistry and Molecular Biology, Inc. (Mar. 2000).
Beaucage, S.L. and Caruthers, M.H., "Deoxynucleoside Phosphoramidites-A New Class of Key Intermediates for Deoxypolynucleotide Synthesis," *Tetra. Lett.* 22:1859-1862, Pergamon Press Ltd. (1981).
Belousov, E.S., et al., "Sequence-specific targeting and covalent modification of human genomic DNA," *Nucl. Acids Res.* 25:3440-3444, Oxford University Press (1997).
Blommers, M.J.J., et al., "Effects of the Introduction of L-Nucleotides into DNA. Solution Structure of the Heterochiral Duplex d(G-C-G-(L)T-G-C-G)•d(C-G-C-A-C-G-C) Studied by NMR Spectroscopy," *Biochem.* 33:7886-7896, American Chemical Society (1994).
Brown, E.L., et al., "Chemical Synthesis and Cloning of a Tyrosine tRNA Gene," *Meth. Enzymol.* 68:109-151, Academic Press (1979).
Caruthers, M.H., et al., "New chemical methods for synthesizing polynucleotides," *Nucl. Acids Res., Symp. Series* No. 7:215-223, Academic Press (1980).
Contag, C.H., et al., "Use of Reporter Genes for Optical Measurements of Neoplastic Disease In Vivo," *Neoplasia* 2:41-52, Nature Publishing Group (Jan.-Apr. 2000).
Döbeli, H., et al., "Recombinant Fusion Proteins for the Industrial Production of Disulfide Bridge Containing Peptides: Purification, Oxidation without Concatamer Formation, and Selective Cleavage," *Prot. Express. Purif.* 12:404-414, Academic Press (1998).
Dormer, R.L., et al., "Preparation and Characterization of Liposomes Containing the $Ca^{2+}$-Activated Photoprotein, Obelin," *Biochim. Et Biophys. Acta* 538:87-105, Elsevier/North-Holland Biomedical Press (1978).
Everett, L.M. and Crabb, D.W., "Sensitivity of virally-driven luciferase reporter plasmids to members of the steroid/thyroid/retinoid family of nuclear receptors," *J. Ster. Biochem. Molec. Biol.* 70:197-201, Pergamon Press (Sep.-Oct. 1999).
Forsberg, G., et al., "An Evaluation of Different Enzymatic Cleavage Methods for Recombinant Fusion Proteins, Applied on Des(1-3)Insulin-Like Growth Factor I," *J. Prot. Chem.* 11:201-211, Plenum Press (1992).
Frenkel, K., et al., "7,12-Dimethylbenz[A]anthracene Induces Oxidative DNA Modification In Vivo," *Free Rad. Biol. & Med.* 19:373-380, Elsevier Science Ltd. (1995).
Gambhir, S.S., et al., "Imaging adenoviral-directed reporter gene expression in living animals with positron emission tomography," *Proc. Natl. Acad. Sci.* USA 96:2333-2338, National Academy of Science (Mar. 1999).
Gambhir, S.S., et al., "Imaging Transgene Expression with Radionuclide Imaging Technologies," *Neoplasia* 2:118-138, Nature America Inc. (Jan.-Apr. 2000).
Gambhir, S.S., et al., "A mutant herpes simplex virus type 1 thymidine kinase reporter gene shows improved sensitivity for imaging reporter gene expression with positron emission tomography," *Proc. Natl. Acad. Sci.* USA 97:2785-2790, National Academy of Sciences (Mar. 2000).
Holmgren, L., et al., "Dormancy of micrometastases: Balanced proliferation and apoptosis in the presence of angiogenesis suppression," *Nat. Med.* 1:149-153, Nature Publishing Co. (1995).
Horn, T., et al., "Synthesis of oligonucleotides on cellulose. Part II: design and synthetic strategy to the synthesis of 22 oligodeoxynucleotides coding for Gastric Inhibitory Polypeptide (GIP)," *Nucl. Acids Res. Symp. Series* No. 7:225-232, IRL Press (1980).
Hruby, V.J., et al., "Synthesis of oligopeptide and peptidomimetic libraries," *Curr. Opin. Chem. Biol.* 1:114-119, Current Biology Ltd. (1997).
Humphreys, D.P., et al., "Improved efficiency of site-specific copper(II) ion-catalysed protein cleavage effected by mutagenesis of cleavage site," *Prot. Eng.* 13:201-206, Oxford University Press (Mar. 2000).
Ikeda, M., et al., "Different DNA Elements Can Modulate the Conformation of Thyroid Hormone Receptor Heterodimer and Its Transcriptional Activity," *J. Biol. Chem.* 271:23096-23104, The American Society for Biochemistry and Molecular Biology (1996).

Illarionov, B.A., et al., "Recombinant Obelin: Cloning and Expression of cDNA, Purification, and Characterization as a Calcium Indicator," *Meth. Enzymol.* 305:223-249, Academic Press (May 2000).

Korsmeyer, S.J., et al., "Bcl-2: B Cell Life, Death and Neoplasia," *Curr. Topics Microbiol. Immunol.* 166:203-207, Springer-Verlag (1990).

Kurose, K., et al., "Bioluminescence of the $Ca^{2+}$-binding photoprotein aequorin after cysteine modification," *Proc. Natl. Acad. Sci. USA* 86:80-84, National Academy of Sciences (1989).

MacLaren, D.C., et al., "PET Imaging of Transgene Expression," *Biol. Psych.* 48:337-348, Elsevier Science Inc. (Sep. 2000).

Mata, J.E., et al., "A Hexameric Phosphorothioate Oligonucleotide Telomerase Inhibitor Arrests Growth of Burkitt's Lymphoma Cells in Vitro and in Vivo," *Toxicol. & Appl. Pharmacol.* 144:189-197, Academic Press (1997).

Merrifield, B., "Concept and Early Development of Solid-Phase Peptide Synthesis," *Meth. Enzymol.* 289:3-13, Academic Press (1997).

Moore, J.T. and Kliewer, S.A., "Use of the nuclear receptor PXR to predict drug interactions," *Toxicol.* 153:1-10, Elsevier Science Ireland Ltd. (Nov. 2000).

Narang, S.A., et al., "Improved Phosphotriester Method for the Synthesis of Gene Fragments," *Meth. Enzymol.* 68:90-98, Academic Press, Inc. (1979).

Nath, R., et al., "Processing of cdk5 Activator p35 to Its Truncated Form (p25) by Calpain in Acutely Injured Neuronal Cells," *Biochem. Biophys. Res. Commun.* 274:16-21 (Jul. 2000).

Østergaard, S. and Holm, A., "Peptomers: A versatile approach for the preparation of diverse combinatorial peptidomimetic bead libraries," *Molec. Div.* 3:17-27, Kluwer Academic Publishers (1997).

Ostresh, J.M., et al., "Generation and Use of Nonsupport-Bound Peptide and Peptidomimetic Combinatorial Libraries," *Meth. Enzymol.* 267:220-234, Academic Press, Inc. (1996).

Pollock, D.P., et al., "Transgenic milk as a method for the production of recombinant antibodies," *J. Immunol. Meth.* 231:147-157, Elsevier Science B.V. (Dec. 1999).

Polyak, S.W., et al., "Introduction of spacer peptides N-terminal to a cleavage recognition motif in recombinant fusion proteins can improve site-specific cleavage," *Prot. Eng.* 10:615-619, Oxford University Press (1997).

Repa, J.J., et al., "Regulation of mouse sterol regulatory element-binding protein-1c gene (SREBP-1c) by oxysterol receptors, LXRα and LXRβ," *Genes & Develop.* 14:2819-2830, Cold Spring Harbor Laboratory Press (Nov. 2000).

Roberge, J.Y., et al., "A Strategy for a Convergent Synthesis of N-Linked Glycopeptides on a Solid Support," *Science* 269:202-204, American Association for the Advancement of Science (1995).

Sala-Newby, G.B., et al., "Imaging bioluminescent indicators shows $Ca^{2+}$ and ATP permeability thresholds in live cells attacked by complement," *Immunol.* 93:601-609, Blackwell Science Ltd. (1998).

Samstag, W., et al., "Synthesis and Properties of New Antisense Oligodeoxynucleotides Containing Benzylphosphonate Linkages," *Antisense & Nucl. Acid Drug Develop.* 6:153-156, Mary Ann Liebert, Inc. (1996).

Schwimmer, J., et al., "A review of the literature for whole-body FDG PET in the management of patients with melanoma," *Quart. J. Nucl. Med.* 44:153-167, Edizioni Minerva Medica (Jun. 2000).

Shimomura, O. and Shimomura, A., "Halistaurin, phialidin and modified forms of aequorin as $Ca^{2+}$ indicator in biological systems," *Biochem. J.* 228:745-749, The Biochemical Society (1985).

Shimomura, O., "Luminescence of Aequorin is Triggered by the Binding of Two Calcium Ions," *Biochem. Biophys. Res. Commun.* 211:359-363, Academic Press, Inc. (1995).

Strauss-Soukup, J.K., et al., "Effects of Neutralization Pattern and Stereochemistry on DNA Bending by Methylphosphonate Substitutions," *Biochem.* 36:8692-8698, American Chemical Society (1997).

Tjuvajev, J.G., et al., "Imaging the Expression of Transfected Genes in Vivo," *Cancer Res.* 55:6126-6132, American Association for Cancer Research, Inc. (1995).

Toell, A., et al., "All natural DR3-type vitamin D response elements show a similar functionality in vitro," *Biochem. J.* 352:301-309, The Biochemical Society (first available online Nov. 2000).

Wang, K.K.W., "Calpain and caspase: can you tell the difference?," *Trends Neurosci.* 23:20-26, Elsevier Science Ltd. (Jan. 2000).

Ward, W.W. and Cormier, M.J., "Extraction of *Renilla*-type luciferin from the calcium-activated photoproteins aequorin, mnemiopsin, and berovin," *Proc. Natl. Acad. Sci. USA* 72:2530-2534, National Academy of Sciences (1975).

Williams, G., et al., "Dissection of the Extracellular Human Interferon γ Receptor α-Chain into two Immunoglobulin-like Domains. Production in an *Escherichia coli* Thioredoxin Gene Fusion Expression System and Recognition by Neutralizing Antibodies," *Biochem.* 34:1787-1797, American Chemical Society (1995).

Yip, D., et al., "Matrix metalloproteinase inhibitors: applications in oncology," *Invest. New Drugs* 17:387-399, Klewer Academic Publishers (Nov. 1999).

Yu, Y., et al., "Quantification of target gene expression by imaging reporter gene expression in living animals," *Nat. Med.* 6:933-937, Nature America Inc. (Aug. 2000).

Zhang, L., et al., "Luciferase activity as a marker of tumor burden and as an indicator of tumor response to antineoplastic therapy In vivo," *Clin. Exp. Metastasis* 12:87-92, Kluwer Academic Publishers (1994).

Zhang, Z., et al., "Presenilins are required for γ-secretase cleavage of β-APP and transmembrane cleavage of Notch-1," *Nat. Cell Biol.* 2:463-465, Nature Publishing Group (Jul. 2000).

Dilber, et al., "Intercellular delivery of thymidine kinase prodrug activating enzyme by the herpes simplex virus protein, VP22," Gene Therapy, 19999, 6, pp. 12-21.

Ehrhard et al., "Use of G-protein fusions to monitor integral membrane protein-protein interactions in yeast," Nature Biotechnology. vol. 8, pp. 1075-1079, Oct. 2000.

* cited by examiner

Control　　Staurosporine

E.R.-Luc

E.R.-DEVD-Luc

E.R.-G$_3$-DEVD-G$_3$-Luc

Caspase 8 and 9 Specific Reporters

FIG. 10

```
GATCCACGAAATGAAATGGGTGCTTCAGGAGACATGAGGGCTGCCAACCTTTGGCCAAGCCCTCTTGTGATTAAGCACACTAAGAAGAACTAAGCCCTGCCTTGTCCTTGACAGCTGACCAG
Asp Pro Arg Asn Glu Met Gly Ala Ser Gly Asp Met Arg Ala Ala Asn Leu Trp Pro Ser Pro Leu Val Ile Lys Lys His Thr Lys Asn Ser Pro Ala Leu Ser Pro Ala Leu Thr Ala Asp Gln
                                                                                                                                                                    120
ATGGTCAGTGCCTTGTTGGATGCTGAACCGCCCATGCTCTATTCTATTCTGAATATGATCCTTCAGTGAAGCCTTGAAGCCTTATTGACCAACCTAGCAGATAGGGAGCTG
Met Val Ser Ala Leu Leu Asp Ala Glu Pro Pro Met Leu Tyr Ser Gly Tyr Asp Pro Ser Arg Pro Phe Ser Glu Ala Ser Met Met Gly Leu Leu Thr Asn Leu Ala Asp Arg Glu Leu
                                                                                                                                                                    240
GTTCATATGATCAACTGGGCAAAGAGAGTGCCAGGCTTTGGGACTTGAATCTCGATCAGGTCCACCTTCTCGAGTGTGCCTGGCTGGAGATTCTGATGATTGGTCTCGTCTGGCGC
Val His Met Ile Asn Trp Ala Lys Arg Val Pro Gly Phe Gly Asp Leu Asn Leu His Asp Gln Val His Leu Leu Glu Cys Ala Trp Leu Glu Ile Leu Met Ile Gly Leu Val Trp Arg
                                                                                                                                                                    360
TCCATGGAACACCCCGGGAAGCTCCTGTTTGCCCCTAACTTGCTCCTGGACAGGAATCAAGGTAAATGTGTGGAAGGCATGGTTGAGATCTTTGACATGTTGCTTGCTACGTCAAGTCGG
Ser Met Glu His Pro Gly Lys Leu Leu Phe Ala Pro Asn Leu Leu Leu Asp Arg Asn Gln Gly Lys Cys Val Glu Gly Met Val Glu Ile Phe Asp Met Leu Leu Ala Thr Ser Ser Arg
                                                                                                                                                                    480
TTCCGCATGATGAATCTGCAGGGTGAAGAGTTTGTGTGCCTCAAATCCATCATTTTGCTTAATTCCGGAGTGTACACCGTTTCTCCAGCACCTTGAAGTCTCTGGAAGAGAAGGACCAC
Phe Arg Met Met Asn Leu Gln Gly Glu Glu Phe Val Cys Leu Lys Ser Ile Ile Leu Leu Asn Ser Gly Val Tyr Thr Phe Leu Ser Ser Thr Leu Lys Ser Leu Glu Glu Lys Asp His
                                                                                                                                                                    600
ATCCACCGTGTCCTGGACAAGATCACAGACACTTTGATCCACCTGATGGCCAAAGCTGGCCTGACTCTGCAGCAGCATCGCCGCCTAGCTCAGCTCCTCTCATTCTTTCCCATATC
Ile His Arg Val Leu Asp Lys Ile Thr Asp Thr Leu Ile His Leu Met Ala Lys Ala Gly Leu Thr Leu Gln Gln His Arg Arg Leu Ala Gln Leu Leu Leu Ile Leu Ser His Ile
                                                                                                                                                                    720
CGGCACATGAGTAACAAAGGCATGGAGCATCTCTACAACATGAAATGCAAGAACGTGGTACCCCTCTACGACCTGCTCCTGGAGATGTTGGATGCCCACCGCCTTCATGCCCCAGCAGT
Arg His Met Ser Asn Lys Gly Met Glu His Leu Tyr Asn Met Lys Cys Lys Asn Val Val Pro Leu Tyr Asp Leu Leu Leu Glu Met Leu Asp Ala His Arg Leu His Ala Pro Ala Ser
                                                                                                                                                                    840
CGCATGGGAGTGCCCCCAGGAGGCCCAGCAGCCCACTTCAGCACATTCCTTACAAACCTACTACATACCCCGAAGCAGAGGGCTTCCCCAACACG
Arg Met Gly Val Pro Pro Glu Glu Pro Ser Gln Thr Gln Leu Ala Thr Thr Ser Ser Thr Ser Ala His Ser Leu Gln Thr Tyr Tyr Ile Pro Pro Glu Ala Gly Gly Phe Pro Asn Thr
                                                                                                                                                                    960
ATCTGAGAATTCC        973
Ile •    Glu Phe
```

COMPOSITIONS AND METHODS FOR DETECTING PROTEOLYTIC ACTIVITY

The present Application is a Divisional of U.S. patent application Ser. No. 09/737,255, filed Dec. 13, 2000 now abandoned.

This invention was made with governmental support under National Cancer Institute Grants R24CA83099, 5P20CA86442, 1P50CA93990, an d1R43CA91448-01 and the Michigan Life Sciences Corridor 1773. The Government may have rights in this invention.

TECHNICAL FIELD

This invention generally pertains to the fields of medicine and non-invasive imaging. The invention provides compositions and methods for non-invasive imaging of enzyme (e.g., protease) activity in cells, tissues, organs and entire bodies in vitro, in vivo and in situ. The imaging can be by computer assisted tomography (CAT), magnetic resonance spectroscopy (MRS), magnetic resonance imaging (MRI), positron emission tomography (PET), single-photon emission computed tomography (SPECT), or bioluminescence imaging (BLI).

BACKGROUND

The revolution in molecular biology along with the nearly completed mapping of the human genome provides an unprecedented opportunity to transform our understanding and treatment of human diseases. Paralleling these discoveries, the imaging sciences have made remarkable advances and have reached a stage in which anatomic and functional imaging can be achieved in vivo at submillimeter resolution in both animals and humans. These developments have created a historic opportunity to non-invasively probe cellular and molecular events associated with the ever-expanding myriad of newly identified pathology-related genes and proteins in vivo in both animals and humans. The revolution in molecular biology has expanded our understanding of the genetics and biochemistry of transformed cells. These tremendous advances have been made largely through studies of cultured cells or ex vivo studies on tumor specimens. However, it is clear that extrapolations between in vitro and in vivo situations do not always hold true. Their exists a significant opportunity to bridge this great divide between in vitro and in vivo studies in research, e.g., cancer therapies, through the development of novel molecular imaging approaches.

For example, research would be aided by in vitro and in vivo imaging of apoptosis, or programmed cell death. Apoptosis is a physiologic process important in the normal development and homeostasis of multicellular organisms. The molecular components comprising the cell death machinery have been identified. Apoptosis can be physiologically activated by the activation of death receptors (Fas, TNFR, DR4, DR5 etc) or when a cell undergoes stress. Growth factor withdrawal, environmental conditions that damage mitochondrial function or homeostasis, DNA damaging events, hypoxia, heat, cold and chemical injury, result in activation of apoptosis.

Lack of balance between apoptosis and proliferation has been implicated in a wide variety of pathologic conditions including stroke, dementia, bone marrow diseases and cancer. In stroke, death of white and gray matter by apoptosis plays a central role in hypoxic-ischemic injury in adults. Because the actual loss of cells in these patients is gradual there may be a therapeutic window wherein pharmacological inhibition of apoptosis may prevent the long term debilitating effects of a stroke. In dementia, neuronal and glial cell apoptosis occurs in AIDS, encephalitis, and in neurodegenerative disorders such as Alzheimer's disease, Parkinson's disease and ALS. The gradual loss of white and gray matter in these disorders is primarily due to apoptosis. In bone marrow diseases, beta-thalasemia, sickle cell disease and aplastic anemia are diseases in which excessive apoptosis within the bone marrow is the central cause of the pathology. The ability to image apoptosis within the marrow would not only facilitate diagnosis of these disorders but would also provide a direct measure of therapeutic efficacy of experimental drugs. Cancer is as much a disease of cell death as one of cell proliferation (see, e.g., Korsmeyer (1990) Curr. Top. Microbiol. Immunol. 166:203). For example, constitutive activation of the anti-apoptotic gene bcl-2 leads to B-cell lymphoma (see, e.g., Holgren (1995) Nature Med. 1:149). It is believed that mutations that attenuate apoptotic responses facilitate neoplastic transformation. The mutations may be allowing the accumulation of other growth-promoting mutations that would otherwise commit a cell to suicide in the absence of external growth cues. Tumor progression may also exert a selective pressure for cells resistant to apoptosis. Evolution toward a "survivor" phenotype may be a product of the hypoxia, nutrient starvation, and falling pH that may be produced as tumor cells outgrow their blood supply. The selective pressure may be especially strong just prior to the "angiogenic switch" when dormant tumor growth is thought to be the result of balanced cellular proliferation and apoptosis (see, e.g., Holgren (1995) supra). The resulting defects in the apoptotic response of tumor cells arising from early events in carcinogenesis or as a result of selective pressures are also thought to contribute to the resistance of tumor cells to cytotoxic therapies.

Currently available techniques for studying apoptosis in vivo, such as in solid tumors, make it difficult to study these problems. Scoring apoptotic indices by morphological criteria is time consuming and requires skilled observers. Specific staining of apoptotic cells, such as the TUNEL method for marking the 3' termini of cleaved DNA, is also time consuming and may have a significant false-positive rate.

SUMMARY

The invention provides compositions and methods for non-invasive imaging of enzyme (e.g., protease) activity in cells, tissues and organs and entire bodies in vitro, in vivo and in situ. Because many enzymes and proteases are specifically associated with certain normal and abnormal conditions and diseases, such as apoptosis and cancer, in vitro, in vivo and in situ imaging of protease activity is useful for identification, targeting, diagnosis and the like. The imaging can be by computer assisted tomography (CAT), magnetic resonance spectroscopy (MRS), magnetic resonance imaging (MRI), positron emission tomography (PET), single-photon emission computed tomography (SPECT), or bioluminescence imaging (BLI).

The invention provides a chimeric polypeptide comprising a first domain comprising a bioluminescent or chemiluminescent polypeptide, or a heterologous kinase, and a second domain comprising at least one silencing moiety, and an endogenous protease cleavage motif positioned between the first and second domains. The ability of the bioluminescent or chemiluminescent polypeptide, or heterologous kinase, to directly or indirectly (e.g., by action on a substrate) generate a signal readable by CAT, MRS, PET, SPECT or BLI or equivalent is completely or substantially suppressed by the "silencing" or "quenching" moiety. Upon cleavage of the endogenous protease cleavage motif, the "silencing" or "quenching" domain no longer suppresses the ability of the bioluminescent or chemiluminescent polypeptide to directly or indirectly generate a readable signal (e.g., by the physical separation of the first and second domains). Accordingly, if an endogenous protease cleavage motif is specific for a particular enzyme (e.g., an endogenous cellular protease), or class of enzymes, then after administration of the chimeric polypeptide of the invention, generation of a readable image indicates the presence of that enzyme in active form.

The invention provides a chimeric polypeptide comprising a first domain comprising a bioluminescent or chemiluminescent polypeptide, or a heterologous kinase, and a second domain comprising at least one silencing moiety, and an endogenous protease cleavage motif positioned between the first and second domains. In various aspects of the chimeric polypeptide of the invention, the chemiluminescent polypeptide comprises luciferase, aequorin, obelin, mnemiopsin or berovin, or equivalents thereof. The bioluminescent or chemiluminescent polypeptide can comprise a green fluorescent protein, an alpha-galactosidase or a chloramphenicol acetyltransferase. The heterologous kinase can comprise a herpes simplex virus-1 thymidine kinase (HSV-1 TK), or equivalents thereof.

In one aspect of the chimeric polypeptide of the invention, the silencing moiety comprises a ligand binding domain, such as a steroid hormone receptor ligand binding domain (e.g., a transcription factor), e.g., an estrogen receptor ligand binding domain, such as one derived from a mouse, e.g., a polypeptide comprising a sequence as set forth in SEQ ID NO:4. The hormone receptor can also be a glucocorticoid receptor, a progesterone receptor, an androgen receptor, a mineralcorticoid receptor, a thyroid hormone receptor, a retinoic acid receptor or a retinoid X receptor ("RXR receptor").

In one aspect of the chimeric polypeptide of the invention, the endogenous protease cleavage motif is specifically cleaved by an endogenous cellular protease. In one aspect, the activity of the endogenous cellular protease is increased or decreased during apoptosis (thus, the rate of digestion, or cleavage, of the endogenous protease cleavage motif by the protease is increased or decreased during apoptosis). The endogenous cellular protease cleavage motif can comprise a caspase recognition motif, including any of the known caspases, e.g., caspases 1 through 10. For example, in one aspect the endogenous cellular protease can comprise caspase 3, caspase 6, caspase 7, procaspase 8, caspase 8, caspase 9, caspase 10. The caspase recognition motif can comprise an amino acid sequence selected from group consisting of DEVD (SEQ ID NO:1), IETD (SEQ ID NO:2) and LEHD (SEQ ID NO:3). The endogenous cellular protease can comprise matrix metalloproteinase (MMP) or gamma-secretase. The endogenous protease cleavage recognition motif can comprise a PACE/furin cleavage recognition motif. The endogenous protease cleavage motif can comprise a metalloprotease cleavage recognition motif, a serine protease cleavage recognition motif, or a gamma-secretase cleavage recognition motif. The endogenous protease recognition motif can further comprise at least one glycine residue flanking the carboxy or amino terminal amino acid of the motif, or both.

In one aspect, the chimeric polypeptide of the invention further comprises a cellular transport sequence. The cellular transport sequence can comprise a herpes simplex virus (HSV) VP-22 sequence (see, e.g., U.S. Pat. No. 6,017,735), or equivalent. The cellular transport sequence can be located between the endogenous protease cleavage motif and the first domain or between the endogenous protease cleavage motif and the second domain.

In one aspect, the chimeric polypeptide of the invention comprises at least about 30 amino acids, at least about 50 amino acids, at least about 100 amino acids or at least about 200 amino acids. The chimeric polypeptide of the invention can be a recombinant fusion protein.

In one aspect, the bioluminescent or chemiluminescent, or the heterologous kinase, domain of the chimeric polypeptide can directly, or by enzymatic reaction with a reagent, generate a molecule that can be imaged, for example, by computer assisted tomography (CAT), magnetic resonance spectroscopy (MRS), magnetic resonance imaging (MRI), positron emission tomography (PET), single-photon emission computed tomography (SPECT), bioluminescence image (BLI) or equivalent.

In one aspect, the bioluminescent or chemiluminescent polypeptide domain is flanked on both sides (i.e., carboxy and amino terminal sides) by a silencing moiety and an endogenous protease cleavage motif is positioned between the bioluminescent or chemiluminescent polypeptide domain and each silencing moiety.

In one aspect, the chemiluminescent polypeptide is luciferase and the silencing domain is an estrogen receptor ligand binding domain. In one aspect, the chimeric polypeptide comprises a luciferase flanked on both sides by an estrogen receptor ligand binding domain and an endogenous protease cleavage motif positioned between the luciferase and the estrogen receptor ligand binding domain.

The invention provides a nucleic acid encoding a chimeric polypeptide of the invention. The invention provides a vector comprising a nucleic acid encoding a polypeptide of the invention. The invention provides a transformed or infected host cell comprising a nucleic acid (or expression cassette, e.g., a vector).

The invention provides a non-human transgenic animal that expresses a chimeric polypeptide comprising a first domain comprising a bioluminescent or chemiluminescent polypeptide, or a heterologous kinase, and a second domain comprising at least one silencing moiety, and an endogenous protease cleavage motif positioned between the first and second domains The invention provides a kit comprising the chimeric polypeptide of the invention or a nucleic acid of the invention (including, e.g., a vector) and instructions for use. The kit can further comprise a substrate for the bioluminescent or chemiluminescent polypeptide or the heterologous kinase. The kit can further comprise instructions for measuring apoptosis in a living subject.

The invention provides a pharmaceutical formulation comprising a chimeric polypeptide and a pharmaceutically acceptable excipient suitable, wherein the chimeric polypeptide comprises a first domain comprising a bioluminescent or chemiluminescent polypeptide, or a heterologous kinase, and a second domain comprising at least one silencing moiety, and an endogenous protease cleavage motif positioned between the first and second domains. The pharmaceutical composition can further comprise a substrate for the bioluminescent or the chemiluminescent polypeptide or the heterologous kinase. In one aspect of the pharmaceutical composition, the chemiluminescent polypeptide is luciferase and the substrate is luciferin. The heterologous kinase can be 8-[18F] fluoroganciclovir (FGCV) and the substrate a herpes simplex virus-1 thymidine kinase (HSV-1 TK).

The pharmaceutical composition of the invention can further comprise a liposome or other detergent or lipid. A substrate for a bioluminescent or a chemiluminescent enzyme can be administered in the same lipid vehicle (e.g., liposome) as the bioluminescent or the chemiluminescent polypeptide, or, it can be administered separately.

The invention provides a method for detecting a protease activity in a sample comprising: (a) contacting a polypeptide with a sample containing or suspected of containing a protease under conditions allowing cleavage of the endogenous protease cleavage motif, wherein the protease is capable of cleaving the endogenous protease cleavage motif, wherein the polypeptide comprises a chimeric polypeptide comprising a first domain comprising a bioluminescent or chemiluminescent polypeptide, or a heterologous kinase, and a second domain comprising at least one silencing moiety, and an endogenous protease cleavage motif positioned between the first and second domains; and, (b) detecting the amount of bioluminescent or a chemiluminescent signal in the sample, thereby detecting a protease activity in the sample. The contacting can be in solution, in solid phase or is in a cell in vitro, in situ, or in vivo. For this and other methods of the invention, the endogenous cellular protease can specifically cleave the endogenous protease cleavage motif. The endogenous cellular protease can comprise a caspase. In one aspect, the endogenous cellular protease comprises a caspase 3, a caspase 6, a caspase 7, a procaspase 8, a caspase 8, a caspase 9, or a caspase 10. In one aspect, the endogenous cellular protease comprises a matrix metalloproteinase (MMP) or a gamma-secretase.

The invention provides a method further comprising providing a substrate for the bioluminescent or chemiluminescent polypeptide, or the heterologous kinase, and administering the substrate before, with or after administration of the bioluminescent or chemiluminescent polypeptide or the heterologous kinase. In one aspect, the chemiluminescent polypeptide is luciferase and the substrate is luciferin. The heterologous kinase can be 8-[18F] fluoroganciclovir (FGCV) and the substrate can be a herpes simplex virus-1 thymidine kinase (HSV-1 TK).

The invention provides a method for identifying the presence of a caspase in a sample comprising (a) contacting a polypeptide with a sample under conditions allowing cleavage of the endogenous protease cleavage motif, wherein the polypeptide comprises a chimeric polypeptide comprising a first domain comprising a bioluminescent or chemiluminescent polypeptide, or a heterologous kinase, and a second domain comprising at least one silencing moiety, and an endogenous protease cleavage motif positioned between the first and second domains, and, the endogenous protease cleavage motif is a cleavage motif specific for the caspase; and, (b) detecting the amount of bioluminescent or a chemiluminescent signal in the sample, thereby identifying the presence of the caspase.

The invention provides a method for detecting apoptosis in a cell comprising (a) contacting a polypeptide with the cell under conditions allowing cleavage of the endogenous protease cleavage motif by a cellular enzyme, wherein the polypeptide comprises a chimeric polypeptide comprising a first domain comprising a bioluminescent or chemiluminescent polypeptide, or a heterologous kinase, and a second domain comprising at least one silencing moiety, and an endogenous protease cleavage motif positioned between the first and second domains, and the endogenous protease cleavage motif is a cleavage motif specific for an enzyme associated with apoptosis; and, (b) detecting the amount of bioluminescent or chemiluminescent signal in the cell, thereby identifying the presence and activity of the apoptosis-associated enzyme and detecting apoptosis. In this, as in all methods of the invention, the contacting can be in a cell, a tissue, an organ or an entire body in vitro, in situ, or in vivo. In alternative aspects, the cell, tissue or organ is undergoing aberrant proliferation or aberrant degeneration. The aberrant proliferation can comprise hyperproliferation. In one aspect, the cell comprises a benign or a metastatic tumor, or a solid tumor.

In one aspect, the aberrant proliferation can comprise deficient proliferation. The aberrant degeneration can comprise decreased cell death or increased cell death.

In the methods of the invention, the amount of bioluminescent or chemiluminescent signal in a cell or tissue or organ or entire body can be imaged by computer assisted tomography (CAT), magnetic resonance spectroscopy (MRS), magnetic resonance imaging (MRI), positron emission tomography (PET), single-photon emission computed tomography (SPECT), bioluminescence image (BLI) or equivalent.

The invention provides a method for detecting apoptosis, or, changes in apoptosis, in a cell (or tissue) comprising: (a) contacting a polypeptide with the cell under conditions allowing cleavage of the endogenous protease cleavage motif by a cellular enzyme, wherein the polypeptide comprises a chimeric polypeptide comprising a first domain comprising a bioluminescent or chemiluminescent polypeptide, or a heterologous kinase, and a second domain comprising at least one silencing moiety, and an endogenous protease cleavage motif positioned between the first and second domains, and the endogenous protease cleavage motif is a cleavage motif specific for an enzyme associated with apoptosis; and, (b) detecting any change in an amount of bioluminescent or chemiluminescent signal in the cell, thereby identifying the presence and activity of the apoptosis-associated enzyme and detecting a change in cell apoptosis. In one aspect, the apoptosis-associated enzyme comprises a caspase, e.g., caspase 3 or caspase 9.

As in all methods of the invention, the contacting can be in a cell, a tissue, an organ or an entire body in vitro, in situ, or in vivo. In one aspect, the tissue can comprise breast, brain, head or neck, eye, nasopharynx, lung, liver, pancreas, kidney, esophagus, stomach, small or large intestine, bladder, rectum, prostate, testicle, ovary, uterus, bone, muscle, skin or blood. The cell can comprise a subject undergoing a therapy that increases or decreases cell proliferation or cell death. In one aspect, the subject has or is at risk of having a cell proliferative disorder or a cell degenerative disorder. The cell proliferative disorder can comprise a cell hyperplasia, such as a cancer, e.g., a lymphoma, a myeloma or a leukemia, a solid tumor, a metastatic tumor, a sarcoma or fibrosarcoma, a glioma or a neuroblastoma.

In one aspect, the cell degenerative disorder is produced by a stroke, a heart attack or a partial or complete arterial obstruction. The cell degenerative disorder can afflicts neural tissue, muscular tissue, cardiac tissue or bone marrow cells. The cell degenerative disorder can be dementia, Alzheimer's disease, Parkinson's disease, ALS, Huntington's disease, Machado-Joseph disease, spino-cerebellar ataxias, Kennedy's disease, muscular dystrophy, multiple sclerosis, beta-thalasemia, sickle cell anemia, aplastic anemia, ischemia/reperfusion injury, rheumatoid arthritis or graft versus host disease.

The invention provides a method for monitoring the effectiveness of a therapy that modulates cell proliferation or cell survival in a subject comprising: (a) contacting a cell, a tissue or an organ in the subject, before therapy, with a polypeptide, under conditions allowing cleavage of the polypeptide by an endogenous cellular protease associated with cell proliferation or cell survival, wherein the polypeptide comprises a chimeric polypeptide comprising a first domain comprising a bioluminescent or chemiluminescent polypeptide, or a heterologous kinase, and a second domain comprising at least one silencing moiety, and an endogenous protease cleavage motif positioned between the first and second domains, and the endogenous protease cleavage motif is a cleavage motif specific for an enzyme associated with cell proliferation or cell survival; (b) detecting the amount of bioluminescent or chemiluminescent signal in the cell, tissue or organ, thereby identifying the presence and activity of the cell proliferation- or cell survival-associated enzyme; (c) administering a therapy to the subject; and, (d) detecting any change in the amount of bioluminescent or chemiluminescent signal in the cell, tissue or organ after the therapy, wherein a change in the amount of bioluminescent or chemiluminescent signal after the therapy indicates the amount of cell proliferation or cell survival, thereby indicating the effectiveness of the therapy.

In one aspect, the methods of the invention further comprise re-contacting the cell, tissue or organ with a polypeptide of the invention after administering the therapy to the subject. The effectiveness of the therapy is indicated by an increase, a decrease, in the bioluminescent or chemiluminescent signal after the therapy; thus allowing detection of apoptosis, or, changes in rates of apoptosis or locations of apoptotic events, in cells or tissues. In the methods of the invention, the therapy can inhibit cell proliferation, or the therapy can stimulate cell death, or the therapy can stimulate cell proliferation, or the therapy can inhibit cell death. In the methods of the invention, the therapy can comprise anticancer therapy. The therapy can comprise chemotherapy or radiation therapy. The therapy can comprise treatment (i.e., amelioration) of a cell degenerative disorder, such as a disorder afflicting neural tissue, muscle tissue, cardiac tissue or bone marrow cells. The therapy can comprise treatment (i.e., amelioration) of ischemia, stroke, a heart attack or a partial or complete arterial obstruction, or dementia, Alzheimer's disease, Parkinson's disease, ALS, Huntington's disease, Machado-Joseph disease, spino-cerebellar ataxias, Kennedy's disease, muscular dystrophy, multiple sclerosis, beta-thalasemia, sickle cell anemia, aplastic anemia, ischemia/reperfusion injury, rheumatoid arthritis and graft versus host disease.

The invention provides a computer-implemented method for monitoring relative effectiveness of a therapy that modulates cell proliferation or cell survival in a subject comprising: (a) providing an imaging device in operable association with a computer, (b) taking an image of a defined area of the subject before or during therapy in which the area has been contacted with a polypeptide of the invention to image the amount of bioluminescent or chemiluminescent signal, wherein the endogenous protease cleavage motif of the polypeptide is an endogenous cleavage motif specific for an enzyme associated with cell proliferation or cell survival; (c) outputting the image data to the computer; (d) administering a therapy to the subject and taking another image of the defined area; (e) comparing the image data obtained in step (b) with the image data obtained in step (d) with the computer to generate a differential histogram; and (g) analyzing the differential histogram to quantitate any change in bioluminescent or chemiluminescent signal after therapy, wherein a change in the amount or activity of the bioluminescent or chemiluminescent signal after the therapy indicates a relative effectiveness (or ineffectiveness) of the therapy in modulating cell proliferation or cell survival. The imaging device can be a computer assisted tomography (CAT) device, a magnetic resonance spectroscopy (MRS) device, a magnetic resonance imaging (MRI) device, a positron emission tomography (PET) device, a single-photon emission computed tomography (SPECT) device, a bioluminescence imaging (BLI) device or equivalent. The polypeptide of the invention (and, if appropriate, its substrate) can be administered two or more (several) times, e.g., it can be re-administered several times before a first imaging or after a first imaging.

The invention provides a method for identifying an agent that modulates an enzyme activity comprising: (a) contacting a sample comprising the enzyme with a polypeptide of the invention in the presence and absence of a test agent, wherein the endogenous cleavage motif is an endogenous cleavage motif specific for the enzyme; and, (b) measuring the amount of bioluminescent or chemiluminescent signal in the sample after adding the polypeptide and in the presence and absence of the test agent, wherein an increase or decrease in the amount or activity of the bioluminescent or chemiluminescent signal in the presence of the test agent identifies the test agent as a modulator of the enzyme's activity. In alternative aspects, the contacting between the test agent and the sample can occur in solution or in solid phase, or, it can occur in a cell. The cell can further comprise a tissue, an organ or an entire body. The cell can further comprise a non-human transgenic animal, such as a mouse or a rat, or other animal, as described below.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

FIG. 10 shows an exemplary "silencing domain" of the invention, a mouse estrogen receptor regulatory domain (ER) (SEQ ID NO:4).

Like reference symbols in the various drawings indicate like elements.

DETAILED DESCRIPTION

Figure 1:
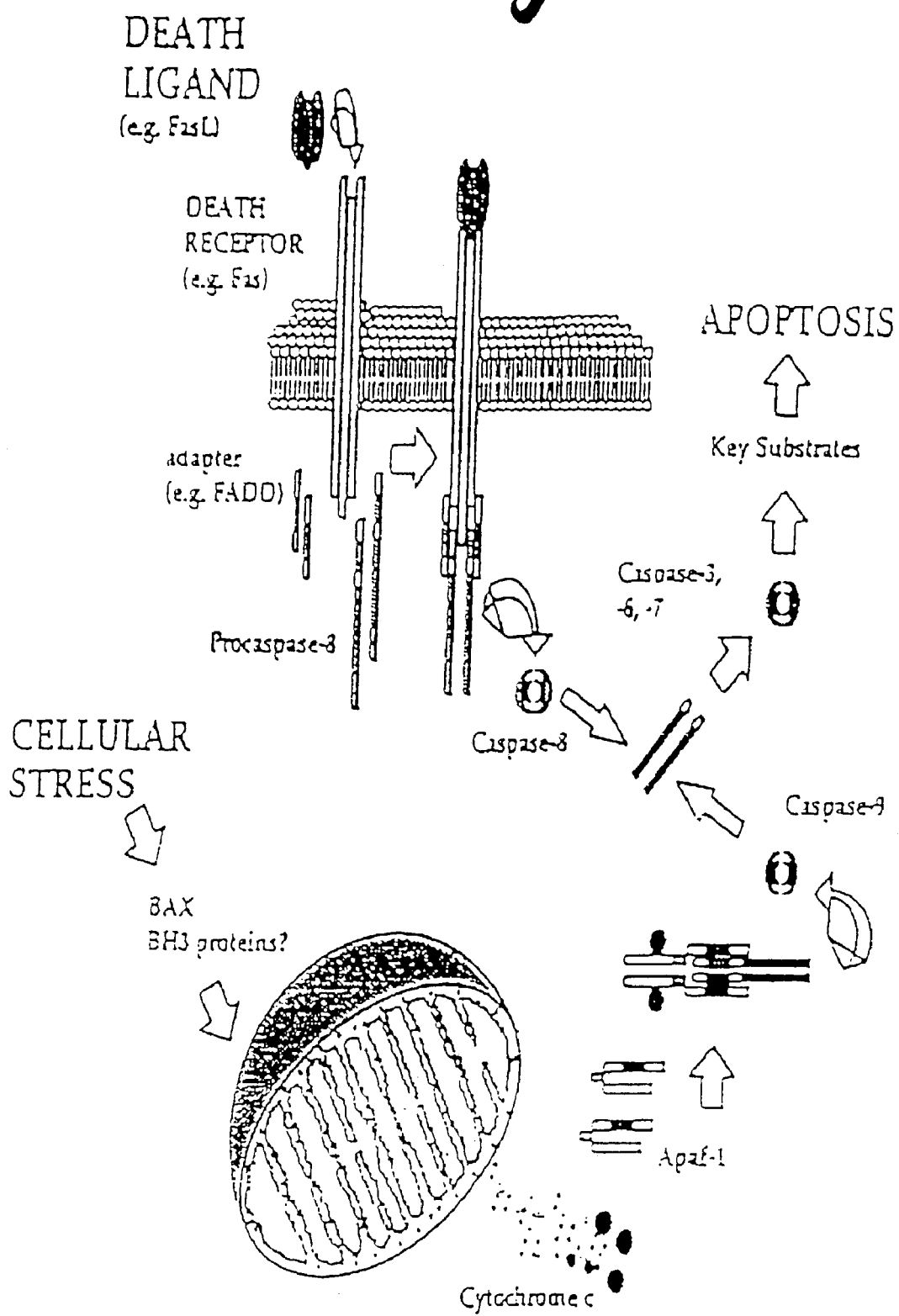
FIG. 1 is a schematic showing apoptosis-associated enzymes, as described in detail in Example 1, below.

The invention provides chimeric polypeptides and methods for using them to non-invasively image enzyme (e.g., protease) activity in vitro, in vivo and in situ. The non-invasive imaging can be in cells, tissues and organs and entire bodies. Because many enzymes and proteases are specifically associated with certain normal and abnormal conditions and diseases, such as cell proliferation, cell death (e.g., apoptosis), cancer, and other diseases, infections and conditions, in vitro, in vivo and in situ imaging of enzyme (e.g., protease) activity is useful for identification, targeting, diagnosis and the like. The imaging can be by computer assisted tomography (CAT), magnetic resonance spectroscopy (MRS), magnetic resonance imaging (MRI), positron emission tomography (PET), single-photon emission computed tomography (SPECT), or bioluminescence imaging (BLI).

Definitions

Unless defined otherwise, all technical and scientific terms used herein have the meaning commonly understood by a person skilled in the art to which this invention belongs. As used herein, the following terms have the meanings ascribed to them unless specified otherwise.

"Caspase-3" or "CPP32" is a mammalian homolog of the *C. elegans* death effector Ced-3. Caspase-3 cleaves a number of enzymes and structural proteins containing the DEVD (SEQ ID NO:1) consensus cleavage site. Cleavage of these "death substrates" commits cells to suicide, and thus caspase-3 is thought to be an end-effector in the caspase cascade induced by apoptotic stimuli.

The term "non-endogenous kinase" or "heterologous kinase" means a kinase not normally associated with a cell or tissue, as described in further detail, below. In some aspects, an exemplary kinase used in the compositions and methods of the invention includes herpes simplex virus-1 thymidine kinase (HSV-1 TK). For example, in the methods of the invention a chimeric polypeptide comprising a domain comprising a non-mammalian kinase is administered to a mammal, e.g., a human.

As used herein, "matrix metalloproteinase (MMP)" includes interstitial collagenases, stromelysins, gelatinases and membrane-type metalloproteinases and MMPs secreted by cancer cells. See, e.g., Yip (1999) Invest. New Drugs 17:387-399.

As used herein, the term "bioluminescence imaging" or "BLI" includes all bioluminescence, fluorescence or chemi-luminescence or other photon detection systems and devices capable of detecting bioluminescence, fluorescence or chemiluminescence or other photon detection systems. Since light can be transmitted through mammalian tissues at a low level, bioluminescent and fluorescent proteins can be detected externally using sensitive photon detection systems; see, e.g., Contag (2000) Neoplasia 2:41-52; Zhang (1994) Clin. Exp. Metastasis 12: 87-92. The methods of the invention can be practiced using any such photon detection device, or variation or equivalent thereof, or in conjunction with any known photon detection methodology, including visual imaging. An exemplary photodetector device is an intensified charge-coupled device (ICCD) camera coupled to an image processor. See, e.g., U.S. Pat. No. 5,650,135. Photon detection devices are manufactured by, e.g., Xenogen (Alameda, Calif.) (the Xenogen IVIS™ imaging system); or, Hamamatsu Corp., Bridgewater, N.J.

As used herein, a "computer assisted tomography (CAT)" or a "computerized axial tomography (CAT)" incorporates all computer-assisted tomography imaging systems or equivalents and devices capable of computer assisted tomography imaging. The methods of the invention can be practiced using any such device, or variation of a CAT device or equivalent, or in conjunction with any known CAT methodology. See, e.g., U.S. Pat. Nos. 6,151,377; 5,946,371; 5,446,799; 5,406,479; 5,208,581; 5,109,397. Animal imaging modalities are also included, such as MicroCAT™ (ImTek, Inc., Knoxville, Tenn.).

As used herein, "positron emission tomography imaging (PET)" incorporates all positron emission tomography imaging systems or equivalents and all devices capable of positron emission tomography imaging. The methods of the invention can be practiced using any such device, or variation of a PET device or equivalent, or in conjunction with any known PET methodology. See, e.g., U.S. Pat. Nos. 6,151,377; 6,072,177; 5,900,636; 5,608,221; 5,532,489; 5,272,343; 5,103,098. Animal imaging modalities are included, e.g. micro-PETs (Corcorde Microsystems, Inc.).

As used herein, "single-photon emission computed tomography (SPECT) device" incorporates all single-photon emission computed tomography imaging systems or equivalents and all devices capable of single-photon emission computed tomography imaging. The methods of the invention can be practiced using any such device, or variation of a SPECT device or equivalent, or in conjunction with any known SPECT methodology. See, e.g., U.S. Pat. Nos. 6,115, 446; 6,072,177; 5,608,221; 5,600,145; 5,210,421; 5,103, 098. Animal imaging modalities are also included, such as micro-SPECTs.

As used herein, "magnetic resonance imaging (MRI) device" incorporates all magnetic resonance imaging systems or equivalents and all devices capable of magnetic resonance imaging. The methods of the invention can be practiced using any such device, or variation of an MRI device or equivalent, or in conjunction with any known MRI methodology. In magnetic resonance methods and apparatus a static magnetic field is applied to a tissue or a body under investigation in order to define an equilibrium axis of magnetic alignment in a region of interest. A radio frequency field is then applied to that region in a direction orthogonal to the static magnetic field direction in order to excite magnetic resonance in the region. The resulting radio frequency signals are detected and processed. The exciting radio frequency field is applied. The resulting signals are detected by radio-frequency coils placed adjacent the tissue or area of the body of interest. See, e.g., U.S. Pat. Nos. 6,151,377; 6,144,202; 6,128,522; 6,127,825; 6,121,775; 6,119,032; 6,115,446; 6,111,410; 602,891; 5,555,251; 5,455,512; 5,450,010; 5,378,987; 5,214,382; 5,031,624; 5,207,222; 4,985,678; 4,906,931; 4,558,279. MRI and supporting devices are manufactured by, e.g., Bruker Medical GMBH; Caprius; Esaote Biomedica (Indianapolis, Ind.); Fonar; GE Medical Systems (GEMS); Hitachi Medical Systems America; Intermagnetics General Corporation; Lunar Corp.; MagneVu; Marconi Medicals; Philips Medical Systems; Shimadzu; Siemens; Toshiba America Medical Systems; including imaging systems, by, e.g., Silicon Graphics. Animal imaging modalities are also included, such as micro-MRIs.

As used herein, the terms "computer" and "processor" are used in their broadest general contexts and incorporate all such devices. The methods of the invention can be practiced using any computer/processor and in conjunction with any known software or methodology. For example, a computer/processor can be a conventional general-purpose digital computer, e.g., a personal "workstation" computer, including conventional elements such as microprocessor and data transfer bus. The computer/processor can further include any form of memory elements, such as dynamic random access memory, flash memory or the like, or mass storage such as magnetic disc optional storage.

As used herein, "bioluminescent" and "chemiluminescent" polypeptides include all known polypeptides known to be bioluminescent or chemiluminescent, or, acting as enzymes on a specific substrate (reagent), can generate (by their enzymatic action) a bioluminescent or chemiluminescent molecule. They include, e.g., isolated and recombinant luciferases, aequorin, obelin, mnemiopsin, berovin and variations thereof and combinations thereof, as discussed in detail, below. In some aspects, the bioluminescent or chemiluminescent are enzymes that act on a substrate that reacts with the reagent in situ to generate a molecule that can be imaged. The substrate can be administered before, at the same time (e.g., in the same formulation), or after administration of the chimeric polypeptide (including the enzyme).

The term "pharmaceutical composition" refers to a composition suitable for pharmaceutical use in a subject (including human or veterinary). The pharmaceutical compositions of this invention are formulations that comprise a pharmacologically effective amount of a composition comprising, e.g., a chimeric composition, a recombinant polypeptide, a nucleic acid encoding a chimeric polypeptide of the invention, a vector comprising a nucleic acid of the invention, or a cell of the invention, and a pharmaceutically acceptable carrier. The pharmaceutical formulation of the invention can further comprise a substrate for the bioluminescent or chemiluminescent polypeptide. For example, the chemiluminescent polypeptide can be luciferase and the reagent luciferin. Alternatively, the substrate reagent can be co-administered or administered before or after the chimeric polypeptide (enzyme) formulation.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide.

The term "nucleic acid" or "nucleic acid sequence" refers to a deoxy-ribonucleotide or ribonucleotide oligonucleotide, including single- or double-stranded, or coding or non-coding (e.g., "antisense") forms. The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

The term "expression cassette" refers to any recombinant expression system for the purpose of expressing a nucleic acid sequence of the invention in vitro or in vivo, constitutively or inducibly, in any cell, including, in addition to mammalian cells, insect cells, plant cells, prokaryotic, yeast, fungal or mammalian cells. The term includes linear or circular expression systems. The term includes all vectors. The cassettes can remain episomal or integrate into the host cell genome. The expression cassettes can have the ability to self-replicate or not, i.e., drive only transient expression in a cell. The term includes recombinant expression cassettes that contain only the minimum elements needed for transcription of the recombinant nucleic acid.

As used herein the terms "polypeptide," "protein," and "peptide" are used interchangeably and include compositions of the invention that also include "analogs," or "conservative variants" and "mimetics" (e.g., "peptidomimetics") with structures and activity that substantially correspond to the polypeptides of the invention, including the chimeric polypeptide comprising a bioluminescent or chemiluminescent polypeptide, or a heterologous kinase, and a silencing moiety, and an endogenous protease cleavage motif positioned between the first and second domains. Thus, the terms "conservative variant" or "analog" or "mimetic" also refer to a polypeptide or peptide which has a modified amino acid sequence, such that the change(s) do not substantially alter the polypeptide's (the conservative variant's) structure and/or activity (e.g., binding specificity), as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W); (see also, e.g., Creighton (1984) Proteins, W.H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides of the invention (e.g., ability to be specifically recognized and cleaved by enzymes, including proteases). The mimetic can be either entirely composed of synthetic, non-natural analogues of amino acids, or, is a chimeric molecule of partly natural peptide amino acids and partly non-natural analogs of anino acids. The mimetic can also incorporate any amount of natural amino acid conservative substitutions as long as such substitutions also do not substantially alter the mimetics' structure and/or activity. As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclo-hexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, N.Y.). A polypeptide can also be characterized as a mimetic by containing all or some non-natural residues in place of naturally occurring amino acid residues; non-natural residues are well described in the scientific and patent literature.

Bioluminescent or Chemiluminescent Polypeptides

The invention provides a chimeric polypeptide, e.g., a recombinant polypeptide, and a pharmaceutical composition, comprising a bioluminescent or chemiluminescent polypeptide. As defined above, these polypeptides include enzymes that act on a specific reagent to generate a molecule that can be imaged (e.g., luciferase reacting with luciferin in situ). Once cleaved, the bioluminescent or chemiluminescent domain is "liberated" from its "silencer" to be used as a reporter in quantitative assays to non-invasively image the endogenous enzyme (e.g., protease) activity (the protease specific for the cleavage motif). The kinase activity can be imaged in living animals using MRI, PET, SPECT and the like.

In alternative aspects, these polypeptides include, e.g., luciferase, aequorin, halistaurin, phialidin, obelin, mnemiopsin or berovin, or, equivalent photoproteins, and combinations thereof. The compositions and methods of the invention also include recombinant forms of these polypeptides as recombinant chimeric or "fusion" proteins, including chimeric nucleic acids and constructs encoding them. Methods of making recombinant forms of these polypeptides are well known in the art, e.g., luciferase reporter plasmids are described, e.g., by Everett (1999) J. Steroid Biochem. Mol. Biol. 70:197-201. Sala-Newby (1998) Immunology 93:601-609, described used of a recombinant cytosolic fusion protein of firefly luciferase and aequorin (luciferase-aequorin). The $Ca^{2+}$-activated photoprotein obelin is described by, e.g., Dormer (1978) Biochim. Biophys. Acta 538:87-105; and, recombinant obelin is described by, e.g., Illarionov (2000) Methods Enzymol. 305:223-249. The photoprotein mnemiopsin is described by, e.g., Anctil (1984) Biochem J. 221: 269-272. The monomeric Ca2+-binding protein aequorin is described by, e.g., Kurose (1989) Proc. Natl. Acad. Sci. USA 86:80-84; Shimomura (1995) Biochem. Biophys. Res. Commun. 211:359-363. The aequorin-type photoproteins halistaurin and phialidin are described by, e.g., Shimomura (1985) Biochem J. 228:745-749. Ward (1975) Proc. Natl. Acad. Sci USA 72:2530-2534, describes the purification of mnemiopsin, aequorin and berovin. The recombinant bioluminescent or chemiluminescent chimeric polypeptides of the invention can be made by any method, see, e.g., U.S. Pat. No. 6,087,476, that describes making recombinant, chimeric luminescent proteins. U.S. Pat. Nos. 6,143,50; 6,074,859; 6,074,859, 5,229,285, describe making recombinant luminescent proteins. The bioluminescent or chemiluminescent activity of the chimeric recombinant polypeptides of the invention can be assayed, e.g., using assays described in, e.g., U.S. Pat. Nos. 6,132,983; 6,087,476; 6,060,261; 5,866, 348; 5,094,939; 5,744,320. Various photoproteins that can be used in compositions of the invention are described in, e.g., U.S. Pat. Nos. 5,648,218; 5,360,728; 5,098,828.

Silencing or Quenching Moieties

The invention provides chimeric polypeptides comprising at least one "silencing" or "quenching" moiety. As noted above, in the intact chimeric polypeptide, the "silencing" or "quenching" domain suppresses the activity of the bioluminescent or chemiluminescent domain sufficiently to dampen the signal to unreadable or relatively low levels (the quenching also can be complete). After cleavage of the endogenous protease cleavage motif, the "silencing" or "quenching" is sufficiently lost to increase the bioluminescent or chemiluminescent signal; the loss can be complete, or, just enough to generate a significantly different signal, i.e., a readably different signal, after endogenous protease activity (cleavage of the chimeric polypeptide of the invention). Any "silencing" or "quenching" moiety can be used. For example, a steroid hormone receptor ligand binding domain (e.g., a transcription factor), or, a ligand for a kinase, can serve as a "quenching" moiety. In one aspect, the steroid hormone receptor ligand binding domain is an estrogen receptor regulatory domain (ER), such as one derived from a mouse (SEQ ID NO:4) (see FIG. 10), which can be the "silencing domain" for a variety of bioluminescent or chemiluminescent polypeptides, including, e.g., for the quenching of luciferase or thymidine kinase activity.

In other aspects, the hormone receptor (e.g., a transcription factor) acting as a "silencing" or a "quenching" moiety can also be a glucocorticoid receptor, a progesterone receptor (see, e.g., Bain (2000) J. Biol. Chem. 275:7313-7320), an androgen receptor, a mineralcorticoid receptor, a thyroid hormone receptor (see, e.g., Ikeda (1996) J. Biol. Chem. 271:23096-23104), a retinoic acid receptor, pregnane X receptor ("PXR," see, e.g., Moore (2000) Toxicology 153: 1-10), liver X receptor ("LXR," see, e.g., Repa (2000) Genes Dev. 14:2819-2830), vitamin D(3) receptor ("VDR," see, e.g., Toell (2000) Biochem J. 352:301-309), or a retinoid X receptor ("RXR," see, e.g., Ikeda (1996) supra).

One exemplary chimeric polypeptide of the invention comprises two ER domains, one amino-and another carboxy-terminal to a luciferase, to maximize the silencing efficiency of the ER on the bioluminescent or chemiluminescent polypeptide, e.g., a luciferase. An endogenous protease cleavage recognition site (from, e.g., a caspase) is inserted on either side of the bioluminescent or chemiluminescent polypeptide (e.g., luciferase) such that during induction of apoptosis both the ER sequences would separate from the polypeptide. Glycine spacers can also be included between one, several or all the various domains of the chimeric polypeptide (e.g., ER-DEVD-$G_3$-Luc-$G_3$-DEVD-ER).

Identification of a "silencing" or "quenching" moiety and the capacity of a silencing moiety to "quench" or "silence" the bioluminescence or chemiluminescence of the (uncleaved) chimeric recombinant polypeptides of the invention also can be assayed using assays described in, e.g., U.S. Pat. Nos. 6,132,983; 6,087,476; 6,060,261; 5,866,348; 5,094,939; 5,744,320.

Endogenous Protease Cleavage Motifs

The invention provides chimeric polypeptides comprising at least one endogenous protease cleavage motif. The endogenous protease cleavage motif can be specifically cleaved by an enzyme endogenous to the system studied (e.g., a cell proliferation or cell death-associated protease) or exogenous to the studied cells (e.g., a transfected enzyme). Any of the many known endogenous protease cleavage motifs can be used in the chimeric polypeptide of the invention. Alternatively, entirely synthetic protease cleavage motifs can be devised and incorporated. For example, in one aspect, the endogenous protease cleavage motif is aspartic acid-glutamic acid-valine-aspartic acid (DEVD) (SEQ ID NO:1), which is specifically recognized by the apoptosis-associated enzyme caspase (see, e.g., U.S. Pat. No. 5,976,822). Protease cleavage motifs specific for apoptosis-associated, endogenous cellular proteases include, e.g., caspase 3, caspase 6, caspase 7, procaspase 8, caspase 8, caspase 9, caspase 10, scan be used. For example, the protease cleavage recognition domain for caspase 8, IETD, or isoleucine-glutamic acid-threonine-aspartic acid, (SEQ ID NO:2) and caspase 9, LEHD, or leucine-glutamic acid-histidine-aspartic acid, (SEQ ID NO:3) can be used. For other enzymes associated with apoptosis, see, e.g., U.S. Pat. Nos. 6,143, 522; 6,107,088; 6,072,031; 6,010,853; 5,985,829; 5,955, 429; 5,935,931; 5,858,715; 5,846,768.

Endogenous protease cleavage recognition domains can also be derived from matrix metalloproteinase (MMP) enzymes (see, e.g., U.S. Pat. Nos. 6,140,099; 6,114,568; 6,093,398; 5,595,885); secretins; gamma-secretase associated with Alzheimer's disease (see, e.g., Zhang (2000) Nat. Cell Biol. 2:463-465); calpain proteases (also associated with Alzheimer's disease, see e.g., Nath (2000) Biochem. Biophys. Res. Commun. 274:16-21; Wang (2000) Trends Neurosci. 23:20-26). Other examples include cleavage site recognized by thrombin, H64A subtilisin, and enterokinase described by Forsberg (1992) J. Protein Chem. 11:201-211. Humphreys (2000) Protein Eng. 13:201-206, described an improved efficiency of the site-specific copper (II) ion-catalyzed protein cleavage peptide sequence (N)DKTH(C) effected by mutagenesis of cleavage site. Various virus-specified protease cleavage recognition sites are described in U.S. Pat. No. 4,952,493.

The endogenous protease cleavage motif positioned between the first and second domains of the chimeric polypeptide. In one aspect, the protease cleavage motif is flanked by a "spacer" on one or both sides (i.e., a spacer is between the cleavage motif and either or both the silencing domain and the bioluminescent or chemiluminescent polypeptide domain. The spacer can be, e.g., a poly-glycine moiety. Other "spacers" are known in the art; for example, to improve site-specific cleavage of a methionyl porcine growth hormone [[Met1]-pGH(1-46)-IGF-II] fusion protein by the enzyme H64A subtilisin, Polyak (1997) Protein Eng. 10:615-619, introduced a series of flexible, unstructured spacer peptides N-terminal to the cleavage site.

Non-Endogenous Kinases

The invention provides a chimeric polypeptide comprising a non-endogenous kinase, such as a herpes simplex virus-1 thymidine kinase (HSV-1 TK). Once cleaved, the kinase domain is liberated from its "silencer" to be used as a reporter in quantitative assays to non-invasively image enzyme (e.g., protease) activity (the endogenous protease specific for the cleavage motif). The kinase activity can be imaged in living animals using MRI, PET, SPECT, BLI and the like.

In one aspect, after administration of the chimeric polypeptide of the invention, a kinase substrate (a "reporter probe") is administered, e.g., the positron-emitting 8-[18F] fluoroganciclovir (FGCV). In one aspect, the herpes simplex virus 1 thymidine kinase enzyme (HSV1-TK) is the kinase. Adenovirus-directed hepatic expression of the HSV-1 TK gene in living mice has been shown to be detectable by PET. See, e.g., Tjuvajev (1995) Cancer Res. 55:6126-6132; Gambhir (1999) Proc. Natl. Acad. Sci. USA 96:2333-2338; Gambhir (2000) Proc. Natl. Acad. Sci. USA 97:2785-2790; Gambhir (2000) Neoplasia 2:118-138; MacLaren (2000) Biol. Psychiatry 48:337-348; Schwimmer (2000) Q. J. Nucl. Med. 44:153-167; Yu (2000) Nat. Med. 6:933-937.

In Vivo Bioluminescent Imaging

The invention provides compositions and methods to enhance the imaging of cells and tissues by, e.g., bioluminescence imaging (BLI). In vivo Bioluminescent Imaging (BLI) is a relatively new imaging modality; see discussion above and, e.g., Contag (2000) Neoplasia 2:41-52. This modality consists of the detection of a photoprotein (i.e., an optical reporter), such as luciferase from the firefly, using a sensitive photon detection system. The number of photons emitted from cells expressing the photoprotein (e.g., luciferase) can be quantitatively detected and overlayed (projected) onto a visual picture of the animal (including humans). This imaging approach provides a two-dimensional image data set and thus provides some spatial information as to the origin of the signal within the animal. An exciting aspect of BLI is its excellent sensitivity along with its ability to report on "molecular events" using specifically designed luciferase reporter constructs.

Nanoparticles and Imaging of Brain Tumors

The invention provides pharmaceutical formulations comprising the chimeric polypeptides of the invention that can further comprise imaging contrast agents (see, e.g., U.S. Pat. No. 4,731,239). The pharmaceutical formulations and/ or the contrast agents can be administered by nanoencapsulation, e.g., by hydrogel nanoparticles (and liposomes, which are discussed below). Nanoencapsulation can be used to manipulate the environment surrounding the pharmaceutical formulation and/or the contrast agent. Although the contrast between healthy and abnormal tissues is strong, there exists considerable overlap of magnetic resonance imaging (MRI) $T_1$ and $T_2$ signals in all tissues. This physical property of biological tissues renders necessary the use of contrast agents for adequate resolution of many lesions: in particular, the diffuse margins of some lesions. Contrast agents for magnetic resonance imaging typically affect the protons on adjacent water molecules shortening either the $T_1$ or $T_2$ signals generated in the magnetic field. The most important factor in enhancement of relaxation is the difference between $T_1$ and $T_2$. There must be direct contact between protons and the magneticparts of the contrast agent in order to shorten the $T_1$ component significantly. This effect canbe clearly observed when gadolinium chelates are encapsulated in liposomes with resulting weakening of the $T_1$ signal. Weakening of the $T_1$ signal is thought to be due to the reduced access of water to the cavity of the liposome.

Enhancement of $T_2$ effects, however, requires clustering of the contrast agent and proximity to each other. This clustering of magnetic contrast agent exerts a greater influence over a much larger localized field. Thus incorporation into liposomes increases the proximity of $T_2$ contrast agents and enhances their effectiveness. Incorporation of contrast agents into the body of hydrogel nanoparticles has with it the potential advantages of both immobilizing and clustering the contrast agent and providing a material through which water can freely diffuse.

The pharmaceutical compositions of the invention can further comprise monocrystalline iron oxide nanoparticles (MION), which have been successfully used in a variety of biological and clinical applications. MION has an average diameter of approximately 18 to 24 nm and thus are able to penetrate endothelial fenestrations throughout the body and are cleared through the reticuloendothelial system and are disposed of by hepatic metabolism of iron. MION has excellent contrast characteristics in vivo and out-performs the most effective dendrimer-conjugated contrast agents.

Polypeptides and Peptides

The invention provides a chimeric polypeptide comprising a bioluminescent or chemiluminescent domain or a heterologous kinase, and a second domain comprising at least one silencing moiety, and an endogenous protease cleavage motif positioned between the first and second domains. As noted above, the term polypeptide includes peptides and peptidomimetics, etc. Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art.

Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer). The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman, et al. (Eds) John Wiley & Sons, Inc., NY. Polypeptides incorporating mimetics can also be made using solid phase synthetic procedures, as described, e.g., by Di Marchi, et al., U.S. Pat. No. 5,422,426. Peptides and peptide mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267: 220-234. Modified peptides of the invention can be further produced by chemical modification methods, see, e.g., Belousov (1997) Nucleic Acids Res. 25:3440-3444; Frenkel (1995) Free Radic. Biol. Med. 19:373-380; Blommers (1994) Biochemistry 33:7886-7896.

Peptides and polypeptides of the invention can also be synthesized and expressed as chimeric or "fusion" proteins with one or more additional domains linked thereto for, e.g., to more readily isolate a recombinantly synthesized peptide, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the purification domain and GCA-associated peptide or polypeptide can be useful to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-14). The histidine residues facilitate detection and purification while the enterokinase cleavage site provides a means for purifying the epitope from the remainder of the fusion protein.

Nucleic Acids and Expression Vectors

This invention provides nucleic acids encoding the chimeric polypeptides of the invention. As the genes and expression cassettes (e.g., vectors) of the invention can be made and expressed in vitro or in vivo, the invention provides for a variety of means of making and expressing these genes and vectors. One of skill will recognize that desired phenotypes can be obtained by modulating the expression or activity of the genes and nucleic acids (e.g., promoters) within the expression cassettes of the invention. Any of the known methods described for increasing or decreasing expression or activity can be used for this invention. The invention can be practiced in conjunction with any method or protocol known in the art, which are well described in the scientific and patent literature.

The nucleic acid sequences of the invention and other nucleic acids used to practice this invention, whether RNA, cDNA, genomic DNA, expression cassettes, vectors, viruses or hybrids thereof, may be isolated from a variety of sources, genetically engineered, amplified, and/or expressed recombinantly. Any recombinant expression system can be used, including, in addition to bacterial cells, e.g., mammalian, yeast, insect or plant cell expression systems.

Alternatively, these nucleic acids can be synthesized in vitro by well-known chemical synthesis techniques, as described in, e.g., Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., generating mutations in sequences, subcloning, labeling probes, sequencing, hybridization and the like are well described in the scientific and patent literature, see e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Transgenic Non-Human Animals

The invention provides transgenic non-human animals, e.g., goats, rats and mice, comprising the chimeric nucleic acids of the invention. These animals can be used, e.g., as in vivo models to study apoptosis, or, as models to screen for enzyme activity in vivo. For example, an increase in the activity of an enzyme capable of cleaving the endogenous protease cleavage domain on the in vivo produced chimeric polypeptide can be read by BLI, PET, MRI, etc. As demonstrated in Example 1, below, such transgenic non-human animals are excellent models for imaging apoptosis in vivo by determining the activity of apoptosis-associated enzymes. The coding sequences for the chimeric polypeptides can be designed to be constitutive, or, under the control of tissue-specific, developmental-specific or inducible transcriptional regulatory factors.

Transgenic non-human animals can be designed and generated using any method known in the art; see, e.g., U.S. Pat. Nos. 6,156,952; 6,118,044; 6,111,166; 6,107,541; 5,959,171; 5,922,854; 5,892,070; 5,880,327; 5,891,698; 5,639,940; 5,573,933, describing making and using transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats.

Formulation and Administration Pharmaceuticals

The invention provides pharmaceutical formulations comprising the chimeric molecules of the invention and a pharmaceutically acceptable excipient suitable for administration to image endogenous enzyme (e.g., protease) activity, and methods for making and using these compositions. These pharmaceuticals can be administered by any means in any appropriate formulation. Routine means to determine drug regimens and formulations to practice the methods of the invention are well described in the patent and scientific literature. For example, details on techniques for formulation, dosages, administration and the like are described in, e.g., the latest edition of Remington's Pharmaceutical Sciences, Maack Publishing Co, Easton Pa.

The formulations of the invention can include pharmaceutically acceptable carriers that can contain a physiologically acceptable compound that acts, e.g., to stabilize the composition or to increase or decrease the absorption of the pharmaceutical composition. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of any co-administered agents, or excipients or other stabilizers and/or buffers. Detergents can also used to stabilize the composition or to increase or decrease the absorption of the pharmaceutical composition. Other physiologically acceptable compounds include wetting agents, emulsifying agents, dispersing agents or preservatives that are particularly useful for preventing the growth or action of microorganisms. Various preservatives are well known, e.g., ascorbic acid. One skilled in the art would appreciate that the choice of a pharmaceutically acceptable carrier, including a physiologically acceptable compound depends, e.g., on the route of administration and on the particular physio-chemical characteristics of any co-administered agent.

In one aspect, the composition for administration comprises a chimeric polypeptide of the invention in a pharmaceutically acceptable carrier, e.g., an aqueous carrier. A variety of carriers can be used, e.g., buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration and imaging modality selected.

The pharmaceutical formulations of the invention can be administered in a variety of unit dosage forms, depending upon the particular enzyme-expressing cell or tissue or cancer to be imaged, the general medical condition of each patient, the method of administration, and the like. Details on dosages are well described in the scientific and patent literature, see, e.g., the latest edition of Remington's Pharmaceutical Sciences. The exact amount and concentration of chimeric polypeptide or pharmaceutical of the invention and the amount of formulation in a given dose, or the "effective dose" can be routinely determined by, e.g., the clinician. The "dosing regimen," will depend upon a variety of factors, e.g., whether the enzyme-expressing cell or tissue or tumor to be imaged is disseminated or local, the general state of the patient's health, age and the like. Using guidelines describing alternative dosaging regimens, e.g., from the use of other imaging contrast agents, the skilled artisan can determine by routine trials optimal effective concentrations of pharmaceutical compositions of the invention. The invention is not limited by any particular dosage range.

The pharmaceutical compositions of the invention (e.g., chimeric polypeptides) can be delivered by any means known in the art systemically (e.g., intravenously), regionally, or locally (e.g., intra- or peri-tumoral or intracystic injection, e.g., to image bladder cancer) by, e.g., intraarterial, intratumoral, intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa), intra-tumoral (e.g., transdermal application or local injection). For example, intra-arterial injections can be used to have a "regional effect," e.g., to focus on a specific organ (e.g., brain, liver, spleen, lungs). For example, intra-hepatic artery injection or intra-carotid artery injection. If it is desired to deliver the preparation to the brain, it can be injected into a carotid artery or an artery of the carotid system of arteries (e.g., occipital artery, auricular artery, temporal artery, cerebral artery, maxillary artery, etc.).

The pharmaceutical formulations of the invention can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Therapeutic compositions can also be administered in a lipid formulation, e.g., complexed with liposomes or in lipid/nucleic acid complexes or encapsulated in liposomes, as in immunoliposomes directed to specific cells. These lipid formulations can be administered topically, systemically, or delivered via aerosol. See, e.g., U.S. Pat. Nos. 6,149,937; 6,146,659; 6,143,716; 6,133,243; 6,110,490; 6,083,530; 6,063,400; 6,013,278; 5,958,378; 5,552,157.

Kits

The invention provides kits comprising the compositions, e.g., the pharmaceutical compositions, nucleic acids, expression cassettes, vectors, cells of the invention, to image the activity of endogenous enzymes. The kits also can contain instructional material teaching methodologies, e.g., how and when to administer the pharmaceutical compositions, how to apply the compositions and methods of the invention to imaging systems, e.g., computer assisted tomography (CAT), magnetic resonance spectroscopy (MRS), magnetic resonance imaging (MRI), positron emission tomography (PET), single-photon emission computed tomography (SPECT) or bioluminescence imaging (BLI). Kits containing pharmaceutical preparations (e.g., chimeric polypeptides, expression cassettes, vectors, nucleic acids) can include directions as to indications, dosages, routes and methods of administration, and the like.

EXAMPLES

The following example is offered to illustrate, but not to limit the claimed invention.

Example 1

In Vivo Imaging of Protease Activity

The following example demonstrates use of the compositions and methods of the invention to in vivo image the activity of endogenous enzymes associated with apoptosis, e.g., caspase-3, caspase-8, caspase-9. Specifically, these experiments demonstrate use of the compositions and methods of the invention to measure the induction of apoptosis by quantitative and non-invasive imaging of endogenous enzyme activation.

Caspase-3, an end-effector in the caspase cascade induced by apoptotic stimuli, was imaged in vivo using a chimeric polypeptide of the invention. Its function in the cell's "cell death," or "apoptosis" pathway is shown in FIG. 1. This schematic also illustrates other apoptosis-associated enzymes that can be included in the invention's strategy for the imaging of the activity of these enzymes, and, thus, apoptosis. The chimeric polypeptide of the invention is designed to include the desired cleavage domain; in this example, the protease cleavage domain specific for caspase-3 was used. However, in other exemplary chimeric polypeptides, the protease cleavage domain is specifically cleaved by, e.g., caspase 3, caspase 6, caspase 7, procaspase 8, caspase 8, caspase 9, caspase 10, matrix metalloproteinase (MMP) or gamma-secretase.

For "normal" cells (i.e., cells not undergoing apoptosis), the chimeric polypeptide is not cleaved and the "reporter" domain (in this example, a luciferase enzyme) is not liberated from the "silencing" domain (in this example, an estrogen receptor regulatory domain (ER).

Other "reporters" can be used e.g., as described above, such as HSV TK, a silencing domain, which also can be an estrogen receptor regulatory domain (ER), and PET imaging. While any "quenching" moiety can be used, in this exemplary fusion protein, the estrogen receptor regulatory domain (ER) "silenced" luciferase. Some luciferase activity may be present; however, this amount is sufficiently low such that upon cleavage a detectable change in bioluminescent signal is imaged by BLI.

For cells undergoing apoptosis, caspase-3 enzyme activity increases significantly. This activation of caspase-3 during apoptosis results in cleavage of the chimeric polypeptide of the invention at the protease cleavage domain, in this example, the (SEQ ID NO:1) sequence. This releases luciferase from the silencing effects of the ER. The "unsilenced" luciferase can react with an appropriate substrate, e.g., luciferin, to generate a signal readable by BLI. In one exemplary chimeric polypeptide, glycine residue spacers were used on both sides of the DEVD (SEQ ID NO:1) cleavage sequence.

In this example, BLI was used; it is a very sensitive imaging technique. BLI has an additional advantage of being more cost effective than PET. It does not require a cyclotron run along with radiochemical synthesis. However, PET is useful for obtaining high resolution imaging of in vivo apoptosis.

Using PCR mutagenesis, three versions of the ER-luciferase chimeric molecule was constructed. The first, ER-Luc), is a simple fusion of the coding sequence for the mouse ER (SEQ ID NO:4) (see FIG. 10) to the firefly luciferase complete coding sequence. A second version, ER-DEVD-Luc, contains the DEVD (SEQ ID NO:1) sequence, as described above. This protease cleavage recognition domain was inserted between the ER and the luciferase sequence. A third version, ER-$G_3$-DEVD-$G_3$-Luc, is identical to the second except that it contains three glycine residues amino- and carboxy-terminal to the DEVD (SEQ ID NO:1) sequence. The ER-Luc construct was a negative control; in the absence of a caspase-3 cleavage site there shouldn't be any cleavage of the polypeptide during apoptosis, even in the presence of caspase-3. The ER-DEVD-Luc chimeric polypeptide should be cleaved during apoptosis. The ER-G3-DEVD-G3-Luc molecule, with the glycine residues "spacers," may be less conformationally restrained (e.g., more "floppy") than the ER-DEVD-Luc polypeptide; thus, it would make the DEVD (SEQ ID NO:1) sequence more accessible to caspase-3.

Construction of these fusion constructs involved the use of PCR primers. The ER and luciferase coding sequence were PCR amplified such that the 3' end of the ER coding sequence contained the caspase cleavage site (with or without the glycine spacers) and the 5' end of the luciferase coding sequence. Since the 3' of the ER and the 5' of the luciferase are complimentary, they can be joined in a PCR reaction using the ER 5' primer and the luciferase 3' primer.

Three independent isolates of each construct were characterized to ensure that PCR errors were not been introduced. In addition, a hi-fidelity thermostable polymerase was used. All the constructs were inserted in the bicistronic vector pZ (Genetics Institute, MA). Each the constructs was transfected into 293T cells to ensure that the correct polypeptide was being made (i.e. 60 kDa of Luc+30 kDa of ER=90 kDa) and that it reacted with the appropriate antibodies (luciferase and mouse estrogen receptor specific), indicating that the amino acid sequence generated by the constructs were appropriate.

Figure 2:
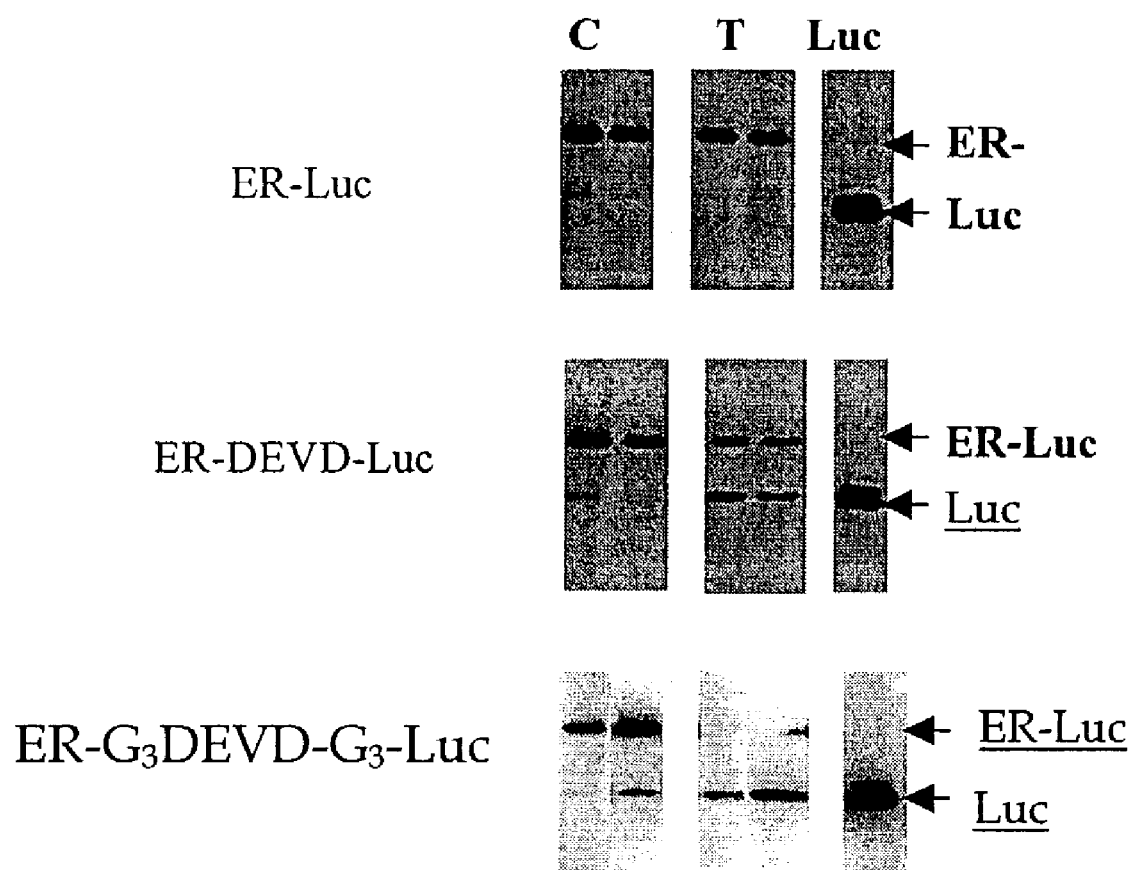
FIG. 2 shows a western blot of extracts from 293T cells transfected with constructs encoding chimeric polypeptides of the invention comprising the caspase 3 protease cleavage recognition domain, with and without glycine "spacers," blotted with a luciferase specific antibody, as described in detail in Example 1, below.

As shown by the western blot illustrated in FIG. 2, after transfection into cells, ER-DEVD-Luc was cleaved in an apoptosis dependent manner. The three constructs described above (two independent clones of each) were transfected into 293T cells. At 48 hr after transfection the cells were either left untreated (lanes labeled C in the figure) or treated with staurosporine to induce apoptosis (labeled T). In an adjacent lane cells transfected with the luciferase (pLuc) expression plasmid were used as control (lane labeled Luc). As shown in the blot, the ER-Luc construct remains as a 90 kDa (60 kDa luc+30 kDa ER) polypeptide under control conditions, as well as under conditions were the cells are undergoing apoptosis. In contrast, while the ER-DEVD-Luc construct is predominantly 90 kDa under control conditions, it is cleaved to yield a 60 kDa polypeptide (luciferase only) when apoptosis is induced. About 50% of the ER-DEVD-Luc protein was cleaved in cells undergoing apoptosis. In contrast, the ER-G3-DEVD-G3-Luc was very efficiently cleaved when apoptosis was induced.

Figure 3:
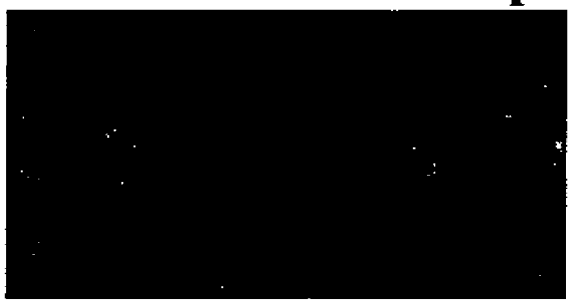
FIG. 3 shows a bioluminescence imaging station reading of 293 cells transfected with various constructs, including two encoding chimeric polypeptides of the invention, as described in detail in Example 1, below.
Figure 3:
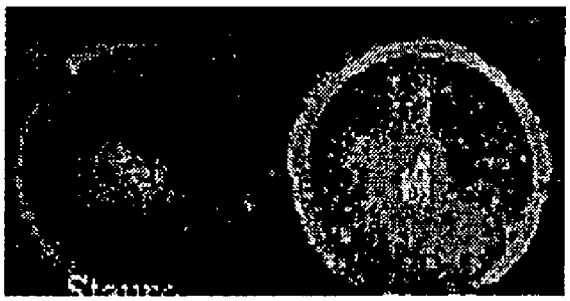
Figure 3:
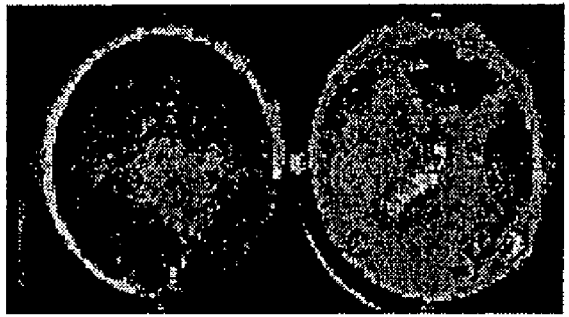

These constructs were next transfected into 293 cells tissue culture cells. FIG. 3 shows a bioluminescence imaging station reading of the transfected cells. Forty-eight hours after transfection cells were left untreated or treated with staurosporine to induce apoptosis. Three hours after treatment the levels of luciferase activity was measured by adding luciferin (0.15 mg/ml) to the tissue culture dish. The cells were then imaged on a bioluminescence imaging station, specifically, the cryogenically-cooled Xenogen IVIS™ (Alameda, Calif.) system coupled to a data acquisition PC running IGOR™ under Windows 98™. This system provides outstanding signal-to-noise images of luciferase signals emerging from within living cells and animals. Cell temperature is regulated using a digitally thermostated stage located in the system. A greyscale image is collected in the chamber followed by acquisition and overlay of a pseudocolor image representing the spatial distribution of photon counts emerging from the active luciferase, e.g., from a multi-well plate or an animal model. Digital image processing software provided by manufacturer, or equivalent, is used to quantitate the photon counts from each digital image data set. The intensity of bioluminescence was represented in the image by pseudo-colors with blue being the least intense, followed by green, yellow and red (although FIG. 3 is in black and white). The release of luciferase from ER correlated with an increase in bioluminescent activity. The data presented here demonstrate that induction of apoptosis results in the activation of luciferase activity in the ER-DEVD-Luc and the ER-G3-DEVD-G3-Luc polypeptide, but not in the molecule that lacks a caspase-3 cleavage site.

Figure 4:
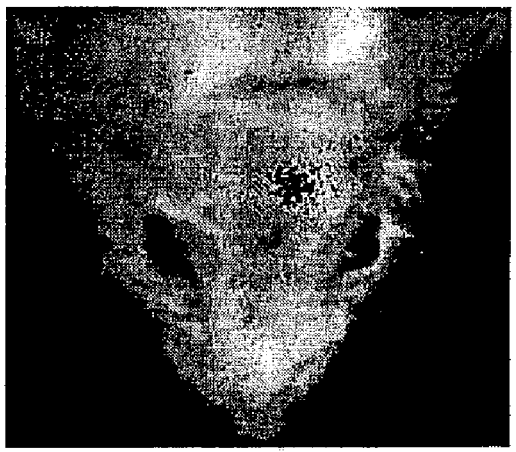
FIG. 4 shows a magnetic resonance image revealing the size and location of the tumor within the brain parenchyma using bioluminescence imaging of cells transfected nucleic acids encoding chimeric polypeptides of the invention, as described in detail in Example 1, below.
Figure 4:
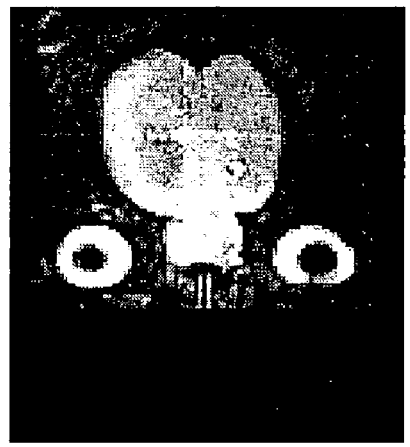

A rat brain tumor cell line that stably expresses luciferase was used to assess the sensitivity of bioluminescence imaging in vivo, as shown in FIG. 4. The right-hand panel shows an MRI image revealing the size and location of the tumor within the brain parenchyma. The image on the left-hand panel reveals the greyscale image of the rat head on which an overlay of the photon counts emitted from the tumor is shown. This data was acquired using a Hamamatsu (Bridgewater, N.J.) image system. A Xenogen system (see above), estimated to have about 100 to 1,000-fold more sensitivity, can also be used. This data reveals for the first time that bioluminescent images (BLI) can be acquired from cells located within the inner regions of a cranium, in this example, a rat skull, thus making the caspase-3 activity imaging method of the invention applicable for the imaging of brain tumors. Tumors as small as 1.5 mm growing in the brain of a rat can be non-invasively imaged in 5 minutes using this approach.

Figure 5:
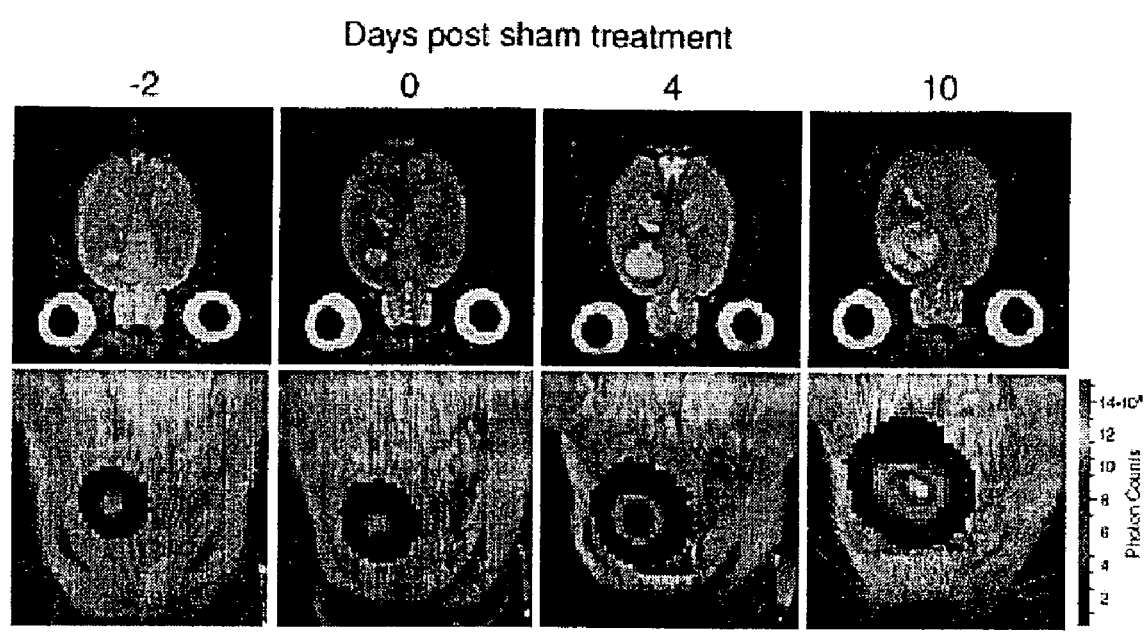
FIG. 5 shows kinetics of intracranial glioma growth in vivo by implanted 9L-Luc (luciferase expressing) cells with MRI (top panel) and BLI (lower panel), as described in detail in Example 1, below.

Next, it was determined that the luciferase-generated signal imaged by the BLI was proportional to the number of cells emitting the signal. A rat with an intracerebral 9L/luciferase-expressing tumor was imaged at three to four day intervals. As shown in FIG. 5, BLI images show the kinetics of intracranial glioma growth in a representative animal. The "9L-Luc" cells were implanted intra-cerebrally at 16 days prior to sham treatment with ethanol vehicle. Tumor progression was monitored with MRI (top panel) and BLI (lower panel). The days, post sham treatment, on which the images were obtained are indicated at the top ("−2" is two days before, "0" is day zero, and 4 days and 10 days after treatment). The MRI images are T2-weighted and are of a representative slice from the multi-slice dataset. The scale to the right of the BLI images describes the color map for the pixel photon counts.

Figure 6:
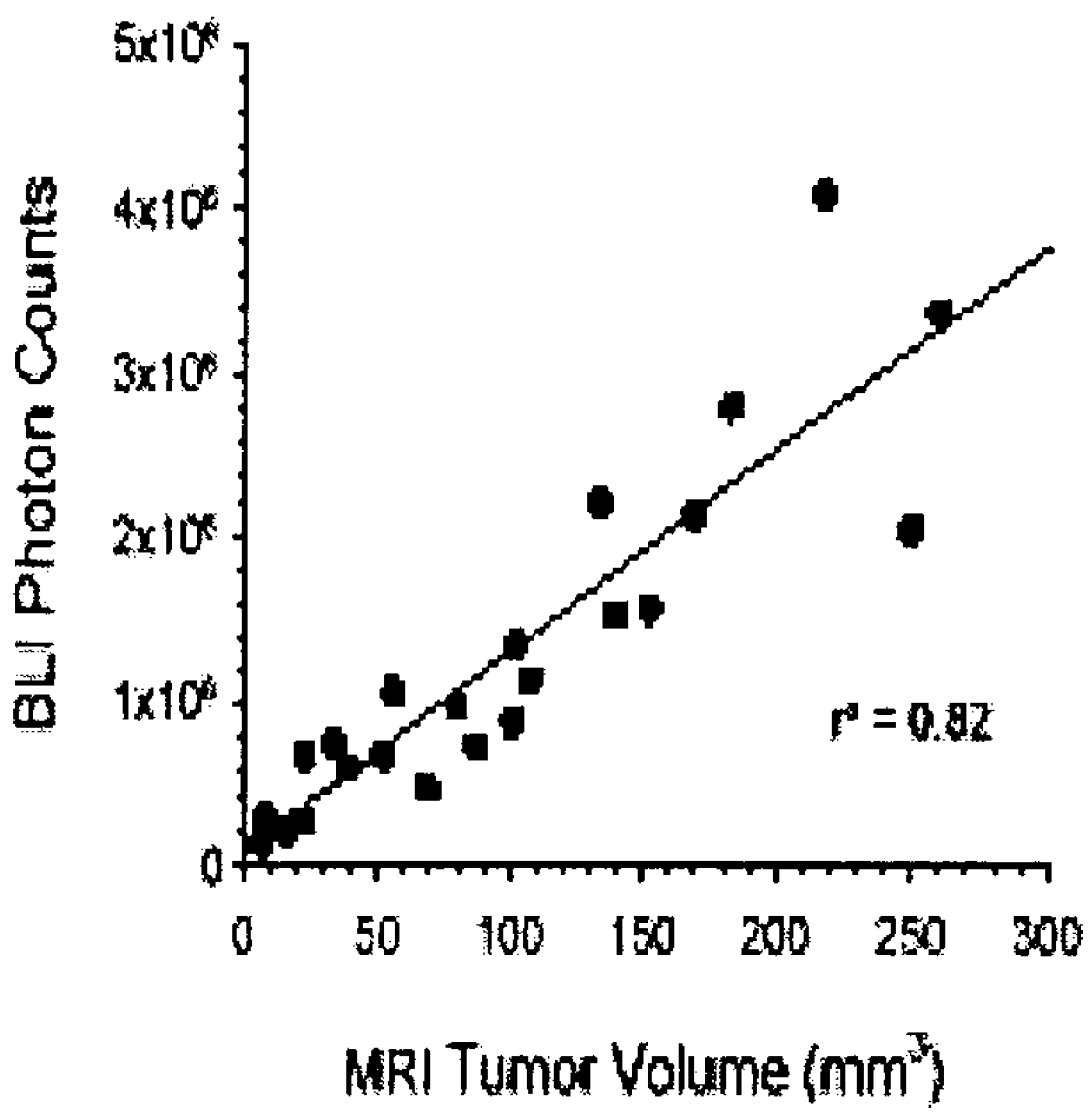
FIG. 6 shows the correlation of tumor volume as measured using BLI with in vivo photon emission as imaged by MRI, as discussed in detail in Example 1, below.

The ability of BLI to determine tumor size was comparable to tumor volume as measured by MRI. The relationship between the two measurements (MRI and BLI) was defined by regression analysis. FIG. 6 shows the correlation of the BLI determined tumor volume with the in vivo photon emission as detected by MRI. The number of cells expressing luciferase was represented by the number of photon counts emerging from the tumor mass. The photon counts from the intracerebral luciferase-expressing tumors were plotted against the MRI-determined tumor volume (units of microliters) from five rats in which data was obtained over time during untreated growth. The amount and size of the bioluminescent signal increased with time as the tumor expanded. There was an excellent correlation of the number of cells expressing luciferase and tumor mass. As indicated by the good correlation coefficient, there was excellent correlation between the BLI and MRI imaging modalities.

This data also demonstrates that, using the compositions and methods of the invention, bioluminescent imaging (BLI) can be used to obtain quantitative data relating to the number of cells expressing caspase 3, i.e., the number of cells undergoing apoptosis. Thus, this approach can provide quantitative data as to the numbers of cells undergoing caspase 3 activation (and apoptosis) within a subject, e.g., a non-human transgenic host animal (e.g., mouse, rat) for study. This is a breakthrough approach for the noninvasive assessment of apoptosis and for quantifying the numbers of cell within a specific organ that have received an apoptotic signaling event. Thus, these methods also provide for the in vivo detection of apoptosis and the screening and testing of novel anti-apoptotic therapeutic strategies in cell and animal models, e.g., transgenic animal.

In order to demonstrate that therapeutic interventions that affect cell numbers relate proportionally to photons emitted, experiments were conducted in which rats harboring intracerebral 9L luciferase-expressing tumors were treated with a chemotherapeutic agent. As the tumor cells begin to die, the amount of light proportionally decreases in response to cell death. In this study, both MRI images and bioluminescent images were acquired in succession over time.

To demonstrate that the compositions (including transgenic non-human animals, such as transgenic mice and rats, expressing the nucleic acids of the invention) and methods of the invention can be applied as in vivo models for screening for novel anti-apoptotic therapeutic agents, experiments were conducted in rats harboring intracerebral 9L luciferase-expressing tumors treated with a known chemotherapeutic agent, the nitrosourea bischloroethylnitrosourea (BCNU, see, e.g., U.S. Pat. Nos. 6,147,060; 5,736,129). As the tumor cells die in response to the BCNU treatment, the amount of light proportionally decreases. Both MRI and BLI images were acquired over various times.

Figure 7:
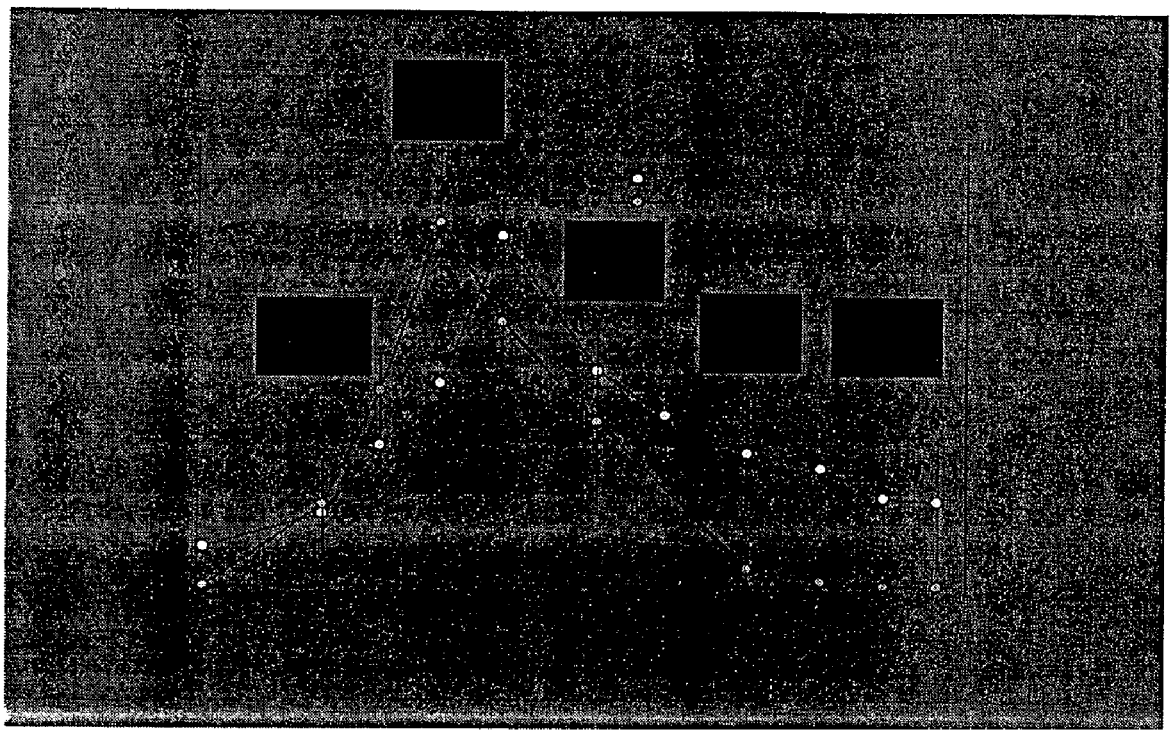
FIG. 7 summarizes data demonstrating that bioluminescence imaging (BLI) can measure events dynamic changes in tumor volume, as discussed in detail in Example 1, below.

FIG. 7 summarizes the data demonstrating that bioluminescence imaging (BLI) can measure events dynamic changes in tumor volume. Three time points were acquired prior to chemotherapy using BCNU, which was administered at time zero. Tumor volume and photon counts continued to increase for three time points after BCNU treatment followed by a decline in both parameters over time. These changes both occurred in a similar time frame and degree of change. Tumor volume and light output should not exactly correlate as the tumor volume becomes non-proportional to living cells following treatment, as it takes time for re-absorption of cellular debris to occur following cell killing. This study clearly demonstrates that the methods of the invention can be used to noninvasively monitor therapeutic intervention of cells with luciferase activity (i.e., cells expressing exogenous luciferase). These data indicate that the invention's novel molecular imaging constructs coupled to a "reporter" (e.g., a luciferase) can be quantitatively and noninvasively imaged to provide dynamic information relating to apoptotic cell death in intact animals, e.g., subjects and non-human transgenic animals.

Figure 8:
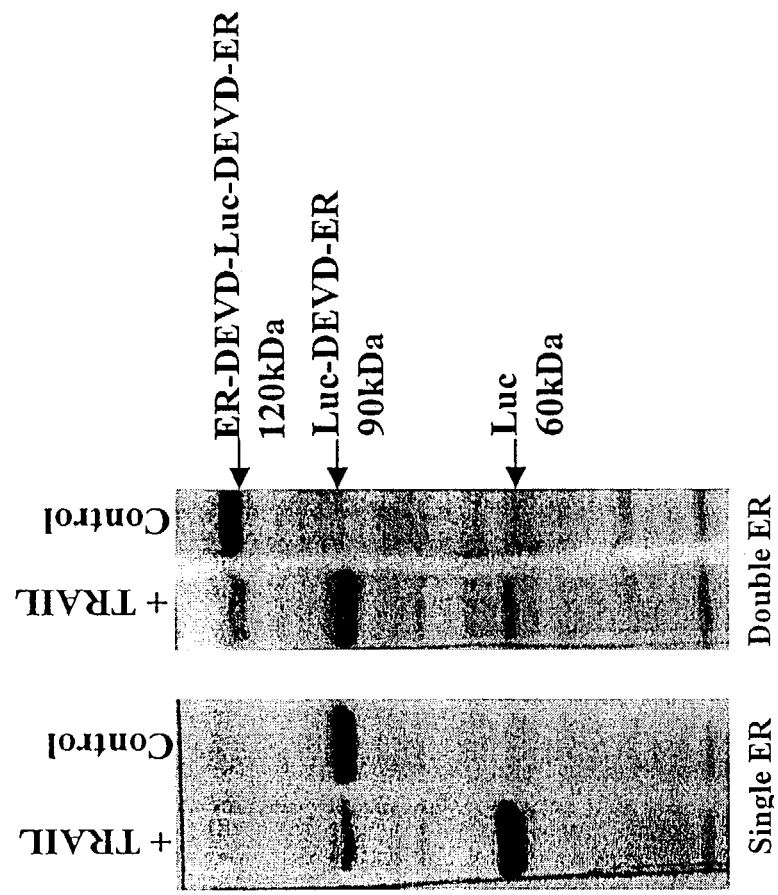
FIG. 8 shows a western blot comparing extracts from 293T cells transfected with constructs encoding chimeric polypeptides of the invention comprising one and two "silencing" domains as described in detail in Example 1, below.

In one aspect of the invention, a chimeric polypeptide comprises two "silencing" domains. The second "silencing domain" maximizes the quenching effect on the bioluminescent or chemiluminescent polypeptide. Experiments to confirm that the constructs are cleaved in an apoptosis-dependent manner were performed by transfection of tissue culture cells with the chimeric polypeptides: ER-DEVD-Luc-DEVD-ER, at 120 kD, and Luc-DEVD-ER, at 90 kD (Luc alone is 60 kD). Tumor necrosis factor-related apoptosis-inducing ligand (TRAIL) was used to induce apoptosis in one set of transformed cells; it is a potent inducer of apoptosis of transformed and cancer cells but not of most normal cells (Ozoren (2000) Cancer Res. 60:6259-6265). FIG. 8 shows a western blot comparing extracts from 293T cells transfected with these constructs. The "control" lane cells were normal, the "+TRAIL" lane cells were induced to undergo apoptosis. The western was blotted with a luciferase specific. As demonstrated by the western blots, endogenous enzymes whose activity is induced by apoptosis can cleave the "double" silencer-containing chimeric polypeptide.

Figure 9:
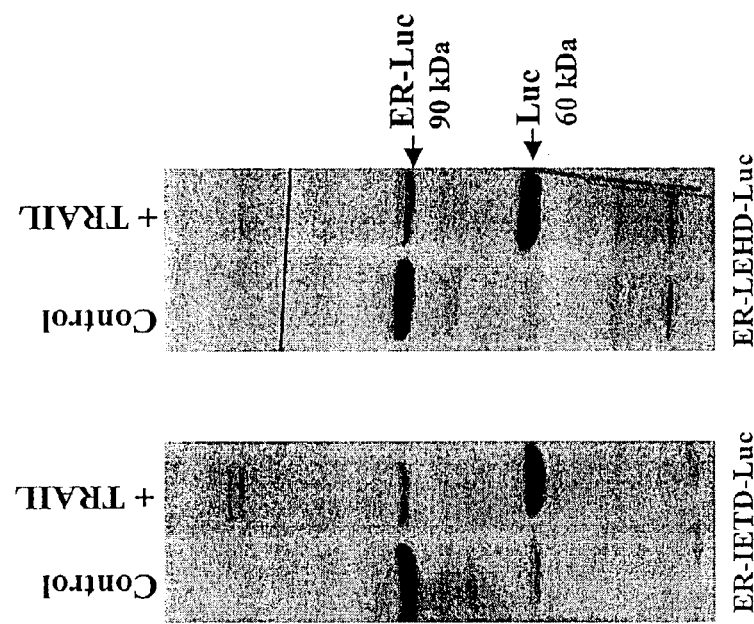
FIG. 9 shows a western blot of extracts from 293T cells transfected with constructs encoding chimeric polypeptides of the invention comprising the caspase 8 and caspase 9 protease cleavage recognition domains, blotted with a luciferase specific antibody, as described in detail in Example 1, below.

In one aspect of the invention, a chimeric polypeptide comprises protease cleavage recognition domains from a caspase, including, e.g., caspase 3, caspase 6, caspase 7, procaspase 8, caspase 8, caspase 9, caspase 10. To confirm that the cleavage recognition domains for the exemplary caspase 8 and caspase 9, which are IETD (SEQ ID NO:2) and LEHD (SEQ ID NO:3), respectively, are cleaved in an apoptosis-dependent manner, experiments were performed by transfection of tissue culture cells with chimeric polypeptides containing these cleavage domains separating Luc from ER. FIG. 9 shows westerns blotted with a luciferase specific antibody of extracts from 293T cells transfected these constructs. As above, TRAIL was used to induce apoptosis. As demonstrated by the western blots, endogenous enzymes whose activity is induced by apoptosis cleave the caspase 8 and caspase 9 cleavage recognition domains.

What is claimed is:

1. A method of imaging, comprising:
   a) providing
      i) cells,
      ii) a mammalian subject, wherein said mammalian subject has endogenous expression of a target caspase,
      iii) a genetic construct, wherein said genetic construct encodes a chimeric polypeptide, where said chimeric polypeptide comprises
         1) an illumination domain
            wherein said illumination domain comprises a bioluminescence imaging unit,
         2) at least two silencing domains, wherein said at least two silencing domains comprise a receptor ligand binding unit, wherein said receptor ligand binding unit is a steroid hormone receptor ligand binding unit, and
         3) a target caspase recognition site,
            wherein said target caspase recognition site is configured to bind whith an endogenous target caspase expressed whithin said subject;
            wherein said target caspase recongnition site comprises a caspase-3 recognition site, wherein said caspase-3 recognition site comprise DEVD; and
      iv) an imaging agent, and
   b) transfecting said cells with said genetic construct;
   c) implanting said cells into said mammalian subject;
   d) administering said imaging agent to said mammalian subject; and
   e) measuring the activity of said endogenous target caspase by detecting signal from said illumination unit.

2. The method of claim 1, wherein said target caspase recognition site is positioned between said illumination domain and said at least two silencing domains.

3. The method of claim 1, wherein said cells are tumor cells.

4. The method of claim 3, wherein said tumor cells are mammalian tumor cells.

5. The method of claim 4, wherein said mammalian tumor cells are rat brain tumor cells.

6. The method of claim 1, wherein said imaging agent is luciferin.

7. The method of claim 1, wherein said bioluminescent imaging unit is a bioluminescent polypeptide.

8. The method of claim 7, wherein said bioluminescent polypeptide is luciferase.

9. The method of claim 1, wherein said bioluminescent imaging unit is a chemiluminescent polypeptide.

10. The method of claim 1, wherein said steroid hormone receptor ligand binding unit is an estrogen receptor regulatory domain (ER).

11. The method of claim 1, wherein said at least two silencing domains are capable of binding with said illumination domain.

12. The method of claim 10, wherein binding of said at least two silencing domains with said illumination domain results in inhibited illumination of said bioluminescent imaging unit.

13. The method of claim 1, wherein said target caspase is capable of binding and cleaving said target caspase recognition site.

14. The method of claim 12, wherein cleaving of said target caspase recognition site results in liberation of said bioluminescent imaging unit.

15. The method of claim 14, wherein said liberation of said bioluminescent imaging unit results in illumination of said bioluminescent imaging unit.

16. The method of claim 15, wherein said illumination of said bioluminescent imaging unit may be imaged.

17. The method of claim 15, wherein said illumination of said bioluminescent imaging unit is indicative of said target caspase activity.

18. The method of claim 17, wherein said target caspase activity is indicatiye of cellular apoptosis.

19. The method of claim 1, wherein said chimeric polypeptide comprises one illumination domain, two target caspase recognition sites, and two silencing domains.

20. The method of claim 19, wherein said illumination domain is luciferase.

21. The method of claim 19, wherein said two target caspase recognition sites comprise the amino acid sequence: DEVD.

22. The method of claim 19, wherein said two silencing domains are estrogen receptors.

23. The method of claim 19, wherein said illumination domain is luciferase, wherein said two target caspase recognition sites comprise the amino acid sequence: DEVD, wherein said two silencing domains are estrogen receptors.

24. The method of claim 1, wherein said mammalian subject is a rodent.

* * * * *

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Asp Glu Val Asp
1

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Ile Glu Thr Asp
1
```

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Leu Glu His Asp
1

<210> SEQ ID NO 4
<211> LENGTH: 973
<212> TYPE: DNA
<213> ORGANISM: Mus musculus
<220> FEATURE:
<221> NAME/KEY: CDS
<222> LOCATION: (1)..(972)

<400> SEQUENCE: 4

```
gat cca cga aat gaa atg ggt gct tca gga gac atg agg gct gcc aac        48
Asp Pro Arg Asn Glu Met Gly Ala Ser Gly Asp Met Arg Ala Ala Asn
1               5                   10                  15 ctt tgg cca agc cct ctt gtg att aag cac act aag aag aat agc cct        96
Leu Trp Pro Ser Pro Leu Val Ile Lys His Thr Lys Lys Asn Ser Pro
            20                  25                  30 gcc ttg tcc ttg aca gct gac cag atg gtc agt gcc ttg ttg gat gct       144
Ala Leu Ser Leu Thr Ala Asp Gln Met Val Ser Ala Leu Leu Asp Ala
        35                  40                  45 gaa ccg ccc atg atc tat tct gaa tat gat cct tct aga ccc ttc agt       192
Glu Pro Pro Met Ile Tyr Ser Glu Tyr Asp Pro Ser Arg Pro Phe Ser
    50                  55                  60 gaa gcc tca atg atg ggc tta ttg acc aac cta gca gat agg gag ctg       240
Glu Ala Ser Met Met Gly Leu Leu Thr Asn Leu Ala Asp Arg Glu Leu
65                  70                  75                  80 gtt cat atg atc aac tgg gca aag aga gtg cca ggc ttt ggg gac ttg       288
Val His Met Ile Asn Trp Ala Lys Arg Val Pro Gly Phe Gly Asp Leu
                85                  90                  95 aat ctc cat gat cag gtc cac ctt ctc gag tgt gcc tgg ctg gag att       336
Asn Leu His Asp Gln Val His Leu Leu Glu Cys Ala Trp Leu Glu Ile
            100                 105                 110 ctg atg att ggt ctc gtc tgg cgc tcc atg gaa cac ccg ggg aag ctc       384
Leu Met Ile Gly Leu Val Trp Arg Ser Met Glu His Pro Gly Lys Leu
        115                 120                 125 ctg ttt gct cct aac ttg ctc ctg gac agg aat caa ggt aaa tgt gtg       432
Leu Phe Ala Pro Asn Leu Leu Leu Asp Arg Asn Gln Gly Lys Cys Val
    130                 135                 140 gaa ggc atg gtg gag atc ttt gac atg ttg ctt gct acg tca agt cgg       480
Glu Gly Met Val Glu Ile Phe Asp Met Leu Leu Ala Thr Ser Ser Arg
145                 150                 155                 160 ttc cgc atg atg aac ctg cag ggt gaa gag ttt gtg tgc ctc aaa tcc       528
Phe Arg Met Met Asn Leu Gln Gly Glu Glu Phe Val Cys Leu Lys Ser
                165                 170                 175 atc att ttg ctt aat tcc gga gtg tac acg ttt ctg tcc agc acc ttg       576
Ile Ile Leu Leu Asn Ser Gly Val Tyr Thr Phe Leu Ser Ser Thr Leu
            180                 185                 190 aag tct ctg gaa gag aag gac cac atc cac cgt gtc ctg gac aag atc       624
Lys Ser Leu Glu Glu Lys Asp His Ile His Arg Val Leu Asp Lys Ile
        195                 200                 205 aca gac act ttg atc cac ctg atg gcc aaa gct ggc ctg act ctg cag       672
Thr Asp Thr Leu Ile His Leu Met Ala Lys Ala Gly Leu Thr Leu Gln
    210                 215                 220
```

```
cag cag cat cgc cgc cta gct cag ctc ctt ctc att ctt tcc cat atc    720
Gln Gln His Arg Arg Leu Ala Gln Leu Leu Leu Ile Leu Ser His Ile
225             230                 235                 240 cgg cac atg agt aac aaa ggc atg gag cat ctc tac aac atg aaa tgc    768
Arg His Met Ser Asn Lys Gly Met Glu His Leu Tyr Asn Met Lys Cys
                245                 250                 255 aag aac gtg gta ccc ctc tat gac ctg ctc ctg gag atg ttg gat gcc    816
Lys Asn Val Val Pro Leu Tyr Asp Leu Leu Leu Glu Met Leu Asp Ala
            260                 265                 270 cac cgc ctt cat gcc cca gcc agt cgc atg gga gtg ccc cca gag gag    864
His Arg Leu His Ala Pro Ala Ser Arg Met Gly Val Pro Pro Glu Glu
        275                 280                 285 ccc agc cag acc cag ctg gcc acc acc agc tcc act tca gca cat tcc    912
Pro Ser Gln Thr Gln Leu Ala Thr Thr Ser Ser Thr Ser Ala His Ser
    290                 295                 300 tta caa acc tac tac ata ccc ccg gaa gca gag ggc ttc ccc aac acg    960
Leu Gln Thr Tyr Tyr Ile Pro Pro Glu Ala Glu Gly Phe Pro Asn Thr
305                 310                 315                 320 atc tga gaa ttc c                                                  973
Ile Glu Phe <210> SEQ ID NO 5
<211> LENGTH: 321
<212> TYPE: PRT
<213> ORGANISM: Mus musculus
<220> FEATURE:
<223> OTHER INFORMATION: Synthetic

<400> SEQUENCE: 5

Asp Pro Arg Asn Glu Met Gly Ala Ser Gly Asp Met Arg Ala Ala Asn
1               5                   10                  15

Leu Trp Pro Ser Pro Leu Val Ile Lys His Thr Lys Lys Asn Ser Pro
            20                  25                  30

Ala Leu Ser Leu Thr Ala Asp Gln Met Val Ser Ala Leu Leu Asp Ala
        35                  40                  45

Glu Pro Pro Met Ile Tyr Ser Glu Tyr Asp Pro Ser Arg Pro Phe Ser
    50                  55                  60

Glu Ala Ser Met Met Gly Leu Leu Thr Asn Leu Ala Asp Arg Glu Leu
65                  70                  75                  80

Val His Met Ile Asn Trp Ala Lys Arg Val Pro Gly Phe Gly Asp Leu
                85                  90                  95

Asn Leu His Asp Gln Val His Leu Leu Glu Cys Ala Trp Leu Glu Ile
            100                 105                 110

Leu Met Ile Gly Leu Val Trp Arg Ser Met Glu His Pro Gly Lys Leu
        115                 120                 125

Leu Phe Ala Pro Asn Leu Leu Leu Asp Arg Asn Gln Gly Lys Cys Val
    130                 135                 140

Glu Gly Met Val Glu Ile Phe Asp Met Leu Leu Ala Thr Ser Ser Arg
145                 150                 155                 160

Phe Arg Met Met Asn Leu Gln Gly Glu Glu Phe Val Cys Leu Lys Ser
                165                 170                 175

Ile Ile Leu Leu Asn Ser Gly Val Tyr Thr Phe Leu Ser Ser Thr Leu
            180                 185                 190

Lys Ser Leu Glu Glu Lys Asp His Ile His Arg Val Leu Asp Lys Ile
        195                 200                 205

Thr Asp Thr Leu Ile His Leu Met Ala Lys Ala Gly Leu Thr Leu Gln
    210                 215                 220
```

-continued

```
Gln Gln His Arg Arg Leu Ala Gln Leu Leu Leu Ile Leu Ser His Ile
225                 230                 235                 240

Arg His Met Ser Asn Lys Gly Met Glu His Leu Tyr Asn Met Lys Cys
            245                 250                 255

Lys Asn Val Val Pro Leu Tyr Asp Leu Leu Leu Glu Met Leu Asp Ala
            260                 265                 270

His Arg Leu His Ala Pro Ala Ser Arg Met Gly Val Pro Pro Glu Glu
            275                 280                 285

Pro Ser Gln Thr Gln Leu Ala Thr Thr Ser Ser Thr Ser Ala His Ser
            290                 295                 300

Leu Gln Thr Tyr Tyr Ile Pro Pro Glu Ala Glu Gly Phe Pro Asn Thr
305                 310                 315                 320

Ile
```